United States Patent
Guerin et al.

(10) Patent No.: US 7,641,703 B2
(45) Date of Patent: Jan. 5, 2010

(54) COMPOSITION FOR THE COLORING OF KERATINOUS FIBERS COMPRISING A HALOCHROMIC COMPOUND AND/OR THE DYE CORRESPONDING TO THIS COMPOUND, AND METHOD OF USE THEREOF

(75) Inventors: Frédéric Guerin, Paris (FR); Alain Lagrange, Coupvray (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/076,566

(22) Filed: Mar. 20, 2008

(65) Prior Publication Data

US 2008/0244838 A1 Oct. 9, 2008

Related U.S. Application Data

(60) Provisional application No. 60/907,401, filed on Mar. 30, 2007.

(30) Foreign Application Priority Data

Mar. 20, 2007 (FR) .................................... 07 53923

(51) Int. Cl.
*A61Q 5/10* (2006.01)
(52) U.S. Cl. .................... 8/405; 8/406; 8/407; 8/435; 8/462; 8/565; 8/566; 8/567; 8/568; 8/570; 8/571; 8/572; 8/573; 8/574; 8/575; 8/576
(58) Field of Classification Search .................... 8/405, 8/406, 407, 435, 462, 565, 566, 567, 568, 8/570, 571, 572, 573, 574, 575, 576
See application file for complete search history.

(56) References Cited

U.S. PATENT DOCUMENTS

| | | | |
|---|---|---|---|
| 3,733,337 A | 5/1973 | Balli et al. | |
| 4,057,562 A | 11/1977 | Balli et al. | |
| 4,119,777 A | 10/1978 | Usui et al. | |
| 4,132,436 A | 1/1979 | Ishige et al. | |
| 4,500,897 A | 2/1985 | Matsuda et al. | |
| 4,524,373 A | 6/1985 | Kondo et al. | |
| 4,536,220 A | 8/1985 | Kondo et al. | |
| 4,629,800 A | 12/1986 | Yonese et al. | |
| 4,803,193 A | 2/1989 | Kanda et al. | |
| 5,395,948 A | 3/1995 | Zink | |
| 5,501,945 A * | 3/1996 | Kanakkanatt | 430/338 |

FOREIGN PATENT DOCUMENTS

DE 4 139 851 A1 12/1990
FR 2 072 022 A5 12/1970
FR 2 197 885 A1 9/1972
FR 2 340 210 A1 2/1976
FR 2 862 530 A1 5/2005
FR 2 862 531 A1 5/2005
FR 2 862 532 A1 5/2005
JP 63 301806 A 8/1988
JP 1208182 * 8/1989
WO WO 00/76466 A1 12/2000

OTHER PUBLICATIONS

STIC Search Report dated Aug. 25, 2008.*
Kurosawa, *Thermosensitively color-changing nail lacquers*, Chemical Abstracts Service (1989), Abstract.
Gunzenhauser et al., *Halochromic Molecules*, 73 Helvetica Chimica Acta 359-79 (1990), Abstract.
Sen et al., *The condensation of esters with resorcinol, dimethylaniline and diethyl-m-aminophenol*, 6 J. Indian Chem. Soc. 557-63 (1929).
French Search Report, mailed Nov. 27, 2007, for FR 0753923.
English language abstract for DE 4 139 851 A1, (1990).
English language abstract for FR 2 197 885 A1, (1972).
English language abstract for FR 2 862 530 A1, (2005).
English language abstract for FR 2 862 531 A1, (2005).
English language abstract for FR 2 862 532 A1, (2005).
English language abstract for JP 63 301806 A, (1988).
English language abstract for WO 00/76466 A1, (2000).

* cited by examiner

*Primary Examiner*—Eisa B Elhilo
(74) *Attorney, Agent, or Firm*—Finnegan, Henderson, Farabow, Garrett & Dunner LLP

(57) ABSTRACT

Disclosed herein is the use, in the coloring of keratinous fibers, such as human keratinous fibers, such as the hair, of a composition comprising at least one compound chosen from the compounds of formula (I) comprising a cyclic group G including a ring H capable of opening, the dyes corresponding to the compounds of formula (I) wherein the ring H is open, and the addition salts thereof:

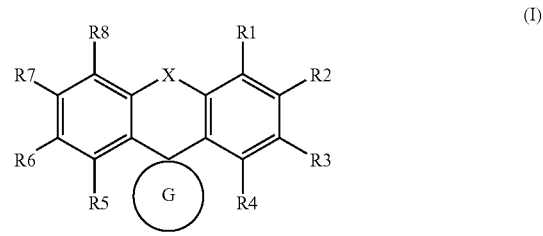

(I)

and a method for treating keratinous fibers employing this composition.

22 Claims, No Drawings

COMPOSITION FOR THE COLORING OF KERATINOUS FIBERS COMPRISING A HALOCHROMIC COMPOUND AND/OR THE DYE CORRESPONDING TO THIS COMPOUND, AND METHOD OF USE THEREOF

This application claims benefit of U.S. Provisional Application No. 60/907,401, filed Mar. 30, 2007, the contents of which are incorporated herein by reference. This application also claims benefit of priority under 35 U.S.C. § 119 to French Patent Application No. FR 0753923, filed Mar. 20, 2007, the contents of which are also incorporated herein by reference.

Disclosed herein is the use, in the coloring of keratinous fibers, such as human keratinous fibers, such as the hair, of a composition comprising at least one suitably selected halochromic compound and/or the dye corresponding to this compound.

It is known to dye keratinous fibers, such as human keratinous fibers, such as the hair, with dyeing compositions comprising oxidation dye precursors, generally known as oxidation bases, such as ortho- or para-phenylenediamines, ortho- or para-aminophenols and heterocyclic compounds, such as diaminopyrazole derivatives. These oxidation bases are colorless or weakly colored compounds which, in combination with oxidizing products, can give rise, by an oxidative coupling process, to colored compounds.

It is also known that it is possible to vary the shades obtained with these oxidation bases by combining them with couplers or coloring modifiers, the latter being chosen, for example, from aromatic meta-diamines, meta-aminophenols, meta-diphenols and certain heterocyclic compounds, such as indole compounds.

The variety of the molecules involved as oxidation bases and couplers makes it possible to obtain a rich palette of colors.

The "permanent" coloring obtained by virtue of these oxidation dyes furthermore has to satisfy a certain number of requirements. Thus, it should be without disadvantage toxicologically, it may make it possible to obtain shades with a desired intensity and it may behave well in the face of external agents, such as light, bad weather, washing, permanent waving, perspiration and rubbing.

The dyes must also make it possible to cover white hair and, finally, be as non-selective as possible, that is to say make it possible to obtain the smallest possible differences in coloring along the same keratinous fiber, which is generally differently sensitized (i.e., damaged) between its tip and its root.

It is also known to dye keratinous fibers, such as human keratinous fibers, such as the hair, with dyeing compositions comprising direct dyes. These dyes are colored and coloring molecules having an affinity for keratinous fibers. They are applied to keratinous fibers for a time necessary for the desired coloring to be obtained and are then rinsed out.

The conventional dyes which are used include dyes of the nitrobenzene, anthraquinone, nitropyridine, azo, cationic azo, xanthene, acridine, azine or triarylmethane type or natural dyes.

Direct dyes are very widely used as they sometimes exhibit certain advantages in comparison with oxidation dye precursors, such as a reduction in potential risks of allergy, the absence of sensitizing of the individual hair due to the oxidation process and shorter development times.

However, the colorations obtained are generally temporary or semi-permanent as the nature of the interactions which bind the direct dyes to the keratinous fiber and their desorption from the surface and/or from the core of this fiber are thought to be responsible for their low dyeing power and for their poor resistance to washing operations, to bad weather or to perspiration. In addition, these direct dyes are generally sensitive to light due to the poor resistance of the chromophore with regard to photochemical attacks and result over time in dulling of the coloring of the hair.

The user can choose the method of coloring which allows him to obtain shades suited to his requirements in terms of highlights and persistence. However, in order to erase the colors thus obtained, it is necessary to use bleaching compositions comprising at least one oxidizing agent or reducing agent of reductone, thiol or sulphite type. Mention may be made, among oxidizing agents conventionally used, of hydrogen peroxide or compounds capable of producing hydrogen peroxide by hydrolysis, such as, for example, urea hydrogen peroxide, or persalts, such as perborates, persulphates or percarbonates. The use of these oxidizing agents can have the disadvantage of resulting in not insignificant damage to the keratinous fibers and of detrimentally affecting their cosmetic properties. The hair has a tendency to become rough, more difficult to disentangle and more brittle. Reducing agents of reductone, thiol or sulphite type for their part exhibit the disadvantage of not being suitable for all types of dyes. While they make it possible to efficiently erase azo dyes without damaging the keratinous fiber, they are ineffective with dyes derived from anthraquinones.

Furthermore, the use in the coloring of keratinous fibers of specific halochromic compounds is known, for example from French Application Publication No. FR 2 862 530, which describes compounds comprising a ring which can undergo opening with the formation of an acid group, from French Application Publication No. FR 2 862 531, which describes compounds comprising a lactone ring, and from French Application Publication No. FR 2 862 532, which describes dimers of compounds comprising a lactone ring. These compounds may make it possible to obtain compositions for the dyeing of keratinous fibers which may make it possible to partially overcome the disadvantages indicated above but which are still insufficiently effective.

Thus, one aspect of the present disclosure is novel halochromic compounds for the dyeing of keratinous fibers which can make it possible to obtain improved compositions for the dyeing of keratinous fibers, such as with regard to the disadvantages mentioned above. Another aspect of the present disclosure is novel halochromic compounds for the dyeing of keratinous fibers which can make it possible to rapidly obtain colorings with intensive and persistent highlights which can be erased using an external agent which does not detrimentally affect the keratinous fibers, such as a pH agent or heat, for example.

Still another aspect of the present disclosure is a composition, and its use thereof in the coloring of keratinous fibers, such as human keratinous fibers, such as the hair, comprising, in a medium appropriate for dyeing, at least one compound chosen from the compounds of formula (I) comprising a cyclic group G including a ring H capable of opening, the dyes corresponding to the compounds of formula (I) wherein the ring H is open and the addition salts thereof:

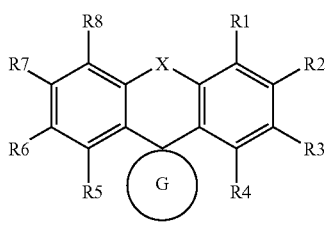

(I)

wherein:

$R_1$, $R_2$, $R_3$, $R_4$, $R_5$, $R_6$, $R_7$ and $R_8$ are chosen from, independently of one another:

hydrogen atoms;

halo radicals;

hydroxyl radicals;

nitro radicals;

amino radicals;

carboxyl radicals;

aminocarbonyl radicals;

cyano radicals;

radicals resulting from a hydrocarbon chain comprising from 1 to 100 carbon atoms, such as from 1 to 50, which is linear or branched, acyclic or mono- or polycyclic, fused or unfused, saturated or unsaturated, aromatic or nonaromatic, which can be interrupted by at least one heteroatom chosen from nitrogen, oxygen and sulphur atoms or by at least one carbonyl group, which can be terminated by a hydrocarbonyl group or by a group comprising at least one heteroatom chosen from nitrogen, oxygen and sulphur atoms, which can begin with a carbonyl group or with a group comprising at least one heteroatom chosen from nitrogen, oxygen and sulphur atoms, and which can be substituted by at least one group chosen from hydroxyl, halo, carboxyl, carboxy ($C_1$-$C_9$)alkyl, cyano, amino and $C_1$-$C_6$ alkoxy radicals;

it being possible for two of the $R_1$, $R_2$, $R_3$, $R_4$, $R_5$, $R_6$, $R_7$ and $R_8$ radicals carried by two adjacent carbon atoms to form, together and with the carbon atoms to which they are attached, a fused or unfused, aromatic, mono- or polycarbocyclic group comprising from 5 to 20 ring members, it being possible for at least one carbon atom to be replaced by an oxygen, nitrogen, sulphur or phosphorus atom, the aromatic mono- or polycarbocyclic group being unsubstituted or substituted by at least one radical chosen from halo, hydroxyl, amino, carboxyl, $C_6$-$C_{18}$ aryl and cyano radicals;

the amino radicals being unsubstituted or substituted by one or two identical or different radicals chosen from $C_1$-$C_9$ alkyl radicals; $C_1$-$C_9$ hydroxyalkyl radicals; $C_2$-$C_9$ alkenyl radicals; $C_6$-$C_{12}$ cycloalkyl radicals; $C_6$-$C_{18}$ aryl radicals optionally substituted by at least one radical chosen from halo and $C_1$-$C_9$ alkyl radicals; ($C_6$-$C_{18}$)arylcarbonyl radicals; cyclo($C_6$-$C_{12}$)alkyl($C_1$-$C_9$)alkyl radicals; ($C_6$-$C_{18}$)aryl($C_1$-$C_9$)alkyl radicals; ($C_1$-$C_9$)alkylcarbonyl radicals; ($C_1$-$C_9$)alkoxycarbonyl($C_1$-$C_9$)alkyl radicals; α-naphthylalkyl radicals; $C_1$-$C_9$ haloalkyl radicals; $C_1$-$C_9$ cyanoalkyl radicals; $C_2$-$C_{15}$ acyl radical; ($C_1$-$C_9$)alkoxycarbonyl radicals; ($C_6$-$C_{18}$)aryloxycarbonyl radicals; ($C_6$-$C_{18}$)aryloxy($C_1$-$C_9$)alkylcarbonyl radicals; ($C_6$-$C_{18}$)aryl($C_1$-$C_9$)alkoxycarbonyl radicals; ($C_1$-$C_9$)alkoxy($C_6$-$C_{18}$)arylcarbonyl radicals; ($C_1$-$C_9$)alkoxy($C_1$-$C_9$)alkylcarbonyl radicals; di($C_1$-$C_9$) alkylaminocarbonyl radicals; di($C_1$-$C_8$)alkylaminosulphonyl radicals; ($C_1$-$C_8$)alkyl($C_6$-$C_{18}$)arylsulphonyl radicals; ($C_1$-$C_9$)alkylsulphonyl radicals; di($C_1$-$C_9$)alkylamino($C_1$-$C_9$) alkyl radicals; and ($C_1$-$C_9$)alkoxy($C_1$-$C_9$)alkyl radicals; it being possible, when the amino radicals are substituted by two radicals, for the latter to form, with the nitrogen atom of the amino radical, a 5- or 6-membered heterocycle optionally comprising at least one additional heteroatom;

X represents a direct bond or a divalent atom, such as a sulphur or oxygen atom, or a sulphone $SO_2$ or $C(R_{13})_2$ or $NR_{13}$ group;

G represents a divalent radical chosen from the formulae G1 to G7:

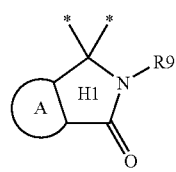

G1

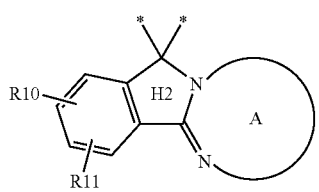

G2

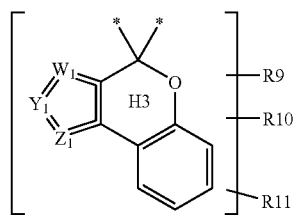

G3

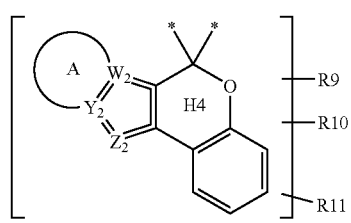

G4

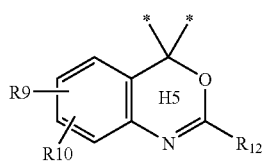

G5

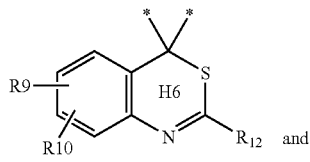

G6 and

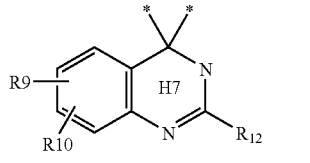

G7 wherein:

$Y_1$, $W_1$ and $Z_1$, on the one hand, and $Y_2$, $W_2$ and $Z_2$, on the other hand, are chosen from, independently of one another, carbon atoms, nitrogen atoms, sulphur atoms and divalent groups $CR_{13}$ or $NR_{13}$;

$R_9$, $R_{10}$, $R_{11}$ and $R_{13}$ have the same definitions as $R_1$;

$R_{12}$ is chosen from:
hydrogen atoms;
$C_1$-$C_9$ alkyl radicals;
amino radicals;
$C_1$-$C_9$ alkoxy radicals;
$C_6$-$C_{18}$ aryl radicals which are unsubstituted or substituted by at least one group chosen from hydrogen atoms, hydroxyl radicals, $C_1$-$C_9$ alkyl radicals, $C_6$-$C_{18}$ aryl radicals, $C_6$-$C_{18}$ aryloxy radicals, $C_1$-$C_9$ alkoxy radicals, halo radicals, carboxyl radicals, cyano radicals and amino radicals which are substituted or unsubstituted;
furanyl radicals;
($C_1$-$C_9$)alkylthio radicals;
thienyl radicals;
phenylcarbonyl radicals;
trifluoroalkyl radicals;
di($C_6$-$C_{18}$)aryl($C_1$-$C_9$)alkyl radicals;

A represents a $C_6$-$C_{18}$ aryl group or a heterocyclic group which is saturated or unsaturated, substituted or unsubstituted, comprising from 5 to 12 ring members.

In one embodiment, the substituents of A, which are identical or different, are of $R_{14}$ type, it being possible for $R_{14}$ to have the same meanings as $R_1$.

Another aspect of the present disclosure is a method for the treatment of keratinous fibers, such as human keratinous fibers, such as the hair, employing the composition in accordance with the disclosure.

The present disclosure may make it possible to rapidly obtain a coloring of keratinous fibers with intense and persistent highlights which can be erased and then reformed just as rapidly. The method for erasing and reforming the color can be repeated at least once without substantial loss of color using a pH agent or by varying the temperature.

The compounds of formula (I) comprise a ring H which can undergo opening with the formation of an acid group in the presence of protons. These compounds are colorless or weakly colored and the compounds corresponding to the opening of the ring H are colored and coloring entities. In an aqueous medium, an equilibrium is established between the colored entities and the colorless entities which depends on the pH and temperature.

When the composition comprises several compounds chosen from the compounds of formula (I), the dyes corresponding to the compounds of formula (I) wherein the ring H is open, and the addition salts thereof, the coloring of the keratinous fibers can also be modified using a pH agent or by varying the temperature.

In the context of the present disclosure, the symbols in the formulae G1 to G7 indicate the bonds via which the divalent radical G is attached to the aromatic nuclei substituted by the $R_1$ to $R_8$ radicals in the formula (I).

In the context of the present disclosure, "alkyl (alk) radical" is understood to mean a linear or branched radical, for example a methyl, ethyl, n-propyl, isopropyl, n-butyl or tert-butyl radical. As used herein an "alkoxy radical" is an alk-O— radical, an "alkylthio radical" is an alk-S— radical, a "mono- or dialkylamino radical" is an —N(alk)$_n$ radical with n=1 or 2, an "alkylcarbonyl radical" is an alk-CO— radical, an "alkoxycarbonyl radical" is an alk-O—CO— radical, an "alkylcarbonylalkyl radical" is an alk-CO-alk- radical and an "alkylcarbonylamino radical" is an alk-CO—NH— radical, the alkyl radical being, in each of these definitions, as defined above.

As used herein, the term "alkenyl radical" is understood to mean an alkyl comprising from 2 to 10 carbon atoms and comprising at least one conjugated or nonconjugated double and/or triple bond.

As used herein, the term "cycloalkyl radical" is understood to mean an alkyl radical wherein the carbon atoms form a ring, for example a cyclohexyl radical. As used herein, a "mono- or dicycloalkylamino radical" is an amino radical substituted by one or two cycloalkyl radicals.

As used herein, the term "aryl (ar) radical" is understood to mean a carbon-comprising radical derived from fused or unfused benzene compounds, for example phenyl, anthracenyl or naphthyl. As used herein, a "mono- or diarylamino radical" is an amino radical substituted by one or two aryl radicals. As used herein, a "mono- or di(arylalkyl)amino radical" is an amino radical substituted by one or two arylalkyl radicals. As used herein, an "arylalkyl radical" is an alkyl radical substituted by an aryl radical. As used herein, an "arylalkoxy radical" is an alkoxy radical substituted by an aryl radical. As used herein, an "arylcarbonyl radical" is an ar-CO— radical wherein ar is as defined above.

As used herein, the term "heteroaryl radical" is understood to mean an aryl radical comprising at least one heteroatom, for example a pyridine ring.

As used herein, "halo radical" is a halogen atom chosen from chlorine, bromine, iodine and fluorine.

As used herein, the term "fused" means at least two rings placed side by side which exhibit at least two atoms in common.

An aromatic or nonaromatic, fused or unfused, mono- or polyheterocyclic group comprising from 5 to 50 ring members can, for example, but not by way of limitation, be a thiophene, benzofuran, benzothiophene, indole, bispyridine, benzopyran, quinoline, pyrazole, pyridine, pyrrole, furan, imidazole or benzimidazole ring.

A fused or unfused aromatic mono- or polycarbocyclic group comprising from 5 to 50 ring members, it being possible for at least one carbon atom to be replaced by an oxygen, nitrogen, sulphur or phosphorus atom, can, for example, but not by way of limitation, be a benzene, naphthalene, anthracene, pyridine, quinoline, thiophene or pyrimidine ring.

As used herein, an "imino radical" is an HN=C radical.

An arylimino radical can, for example, but not by way of limitation, be a phenylimino radical.

As used herein, an "alkoxycarbonylalkylamino radical" is an amino radical substituted by an alkoxycarbonylalkyl radical.

As used herein, an "α-naphthylalkylamino radical" is an amino radical substituted by an α-naphthylalkyl radical, which is an alkyl radical substituted by an α-naphthyl radical.

According to one embodiment of the disclosure, the compound of formula (I) is such that:

$R_1$, $R_4$, $R_5$ and $R_8$ denote a hydrogen atom;

$R_2$ and $R_7$ are chosen from, independently of one another, hydrogen atoms; halo radicals; $C_1$-$C_9$ alkyl radicals; $C_1$-$C_9$ alkoxy radicals; and substituted or unsubstituted amino radicals;

$R_3$ and $R_6$ are chosen from, independently of one another, hydrogen atoms; halo radicals; $C_1$-$C_9$ alkyl radicals; and substituted or unsubstituted amino radicals;

X represents a direct bond or a sulphur or oxygen atom or an $SO_2$ group;

G represents a divalent radical chosen from those of formulae G1, G2, G3, G4, G5 or G6 as defined above.

According to one embodiment of the disclosure, G represents a G1 group; X represents an oxygen atom; $R_1$, $R_3$, $R_4$, $R_5$, $R_6$ and $R_8$ denote a hydrogen atom; $R_2$ and $R_7$ denote, independently of one another, substituted or unsubstituted amino radicals; $R_9$ is chosen from substituted or unsubstituted aryl radicals and substituted or unsubstituted amino radicals; A denotes a substituted or unsubstituted benzene ring.

According to another embodiment of the disclosure, G represents a G2 group; X represents an oxygen atom; $R_1$, $R_3$, $R_4$, $R_5$, $R_6$, $R_8$, $R_{10}$ and $R_{11}$ denote a hydrogen atom; $R_2$ and $R_7$ denote, independently of one another, substituted or unsubstituted amino radicals; A represents a substituted or unsubstituted benzene ring.

According to another embodiment of the disclosure, G represents a G3 group; $R_1$, $R_3$, $R_4$, $R_5$, $R_6$, $R_8$, $R_{10}$ and $R_{11}$ denote a hydrogen atom; $R_2$ or $R_7$ denote, independently of one another, hydrogen atoms and substituted or unsubstituted amino groups; $R_9$ denotes a hydrogen atom, a substituted or unsubstituted alkyl group or an alkoxy group; X represents a direct bond; $W_1$ is chosen from sulphur atoms, carbon atoms substituted by hydrogen atoms, $C_1$-$C_4$ alkyl radicals, phenyl radicals, and amino groups carrying two $C_1$-$C_4$ alkyl groups, the two radicals optionally forming, with the nitrogen atom carrying them, a saturated 5-membered heterocycle; $Y_1$ is chosen from carbon atoms substituted by a hydrogen atom, $C_1$-$C_4$ alkyl radicals, phenyl radicals, amino groups carrying two $C_1$-$C_4$ alkyl groups, the two radicals optionally forming, with the nitrogen atom carrying them, a saturated 5-membered heterocycle, nitrogen atoms, nitrogen atoms substituted by a hydrogen atom, $C_1$-$C_2$ alkyl radicals, phenyl radicals, and phenylalkyl ($C_6H_5$-alkyl-) groups, the alkyl group of which is a $C_1$-$C_4$ alkyl group; $Z_1$ is chosen from nitrogen atoms, nitrogen atoms substituted by a hydrogen atom, $C_1$-$C_2$ alkyl radicals, phenyl radicals, and phenylalkyl ($C_6H_5$-alkyl-) groups, the alkyl group of which is a $C_1$-$C_4$ alkyl group.

According to another embodiment of the disclosure, G represents a G4 group; $R_1$, $R_4$, $R_5$, $R_8$ and $R_{11}$ denote a hydrogen atom; $R_2$ and $R_7$ are chosen from, independently of one another, hydrogen atoms, halogen atoms, alkoxy groups, and substituted or unsubstituted amino groups; $R_3$ and $R_6$ are chosen from, independently of one another, hydrogen atoms, halogen atoms, and substituted or unsubstituted amino groups; $R_9$ is chosen from hydrogen atoms, substituted or unsubstituted alkyl groups, alkoxy groups, aryl groups, and substituted or unsubstituted amino groups; $R_{10}$ is chosen from hydrogen atoms and alkyl radicals; A represents a substituted or unsubstituted benzene ring or a substituted or unsubstituted pyridine ring; X is chosen from oxygen and sulphur atoms, direct bonds and $SO_2$ groups; $W_2$ is chosen from carbon atoms and nitrogen atoms; $Y_2$ is chosen from carbon atoms and nitrogen atoms; $Z_2$ is chosen from CH groups, carbon atoms substituted by hydrogen atoms, $C_1$-$C_4$ alkyl radicals, phenyl radicals, amino groups carrying two $C_1$-$C_4$ alkyl groups, the two radicals optionally forming, with the nitrogen atom carrying them, a saturated 5-membered heterocycle, NH groups, nitrogen atoms, nitrogen atoms substituted by a hydrogen atom, $C_1$-$C_2$ alkyl radicals, phenyl radicals, and phenylalkyl ($C_6H_5$-alkyl-) groups, the alkyl group of which is a $C_1$-$C_4$ alkyl group.

According to another embodiment of the disclosure, G represents a G5 group, X represents an oxygen atom or a direct bond; $R_1$, $R_4$, $R_5$, $R_8$ and $R_{10}$ denote a hydrogen atom; $R_2$ and $R_7$ are chosen from, independently of one another, alkyl radicals, alkoxy radicals, and substituted or unsubstituted amino radicals; $R_3$ and $R_6$ are chosen from, independently of one another, hydrogen atoms, alkyl radicals, and substituted or unsubstituted amino radicals; $R_9$ is chosen from hydrogen atoms and substituted or unsubstituted amino radicals; $R_{12}$ is chosen from substituted or unsubstituted alkyl radicals, substituted or unsubstituted aryl radicals, thienyl radicals, and furanyl radicals.

According to another specific embodiment of the disclosure, G represents a G6 group; X represents a direct bond or an oxygen atom; $R_1$, $R_3$, $R_4$, $R_5$, $R_6$, $R_8$ and $R_{10}$ denote a hydrogen atom, $R_2$, $R_9$ and $R_7$ denote, independently of one another, a substituted or unsubstituted amino group; and $R_{12}$ denotes an alkyl radical.

Non-limiting mention may be made, as examples of compounds of formula (I), of the following compounds:

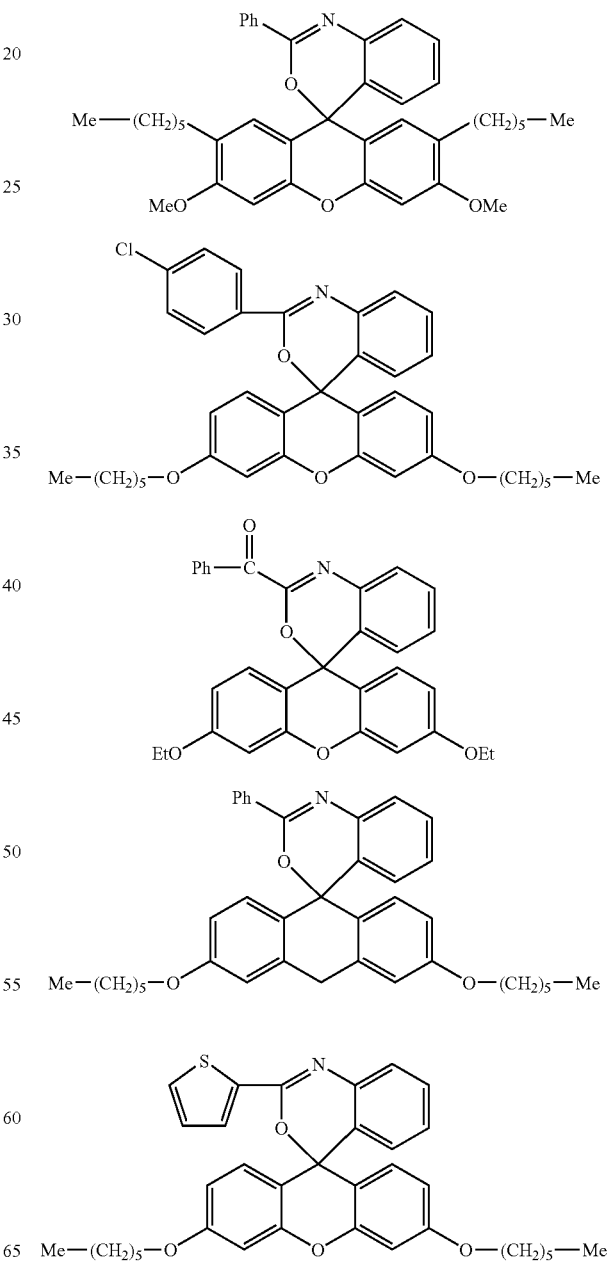

-continued
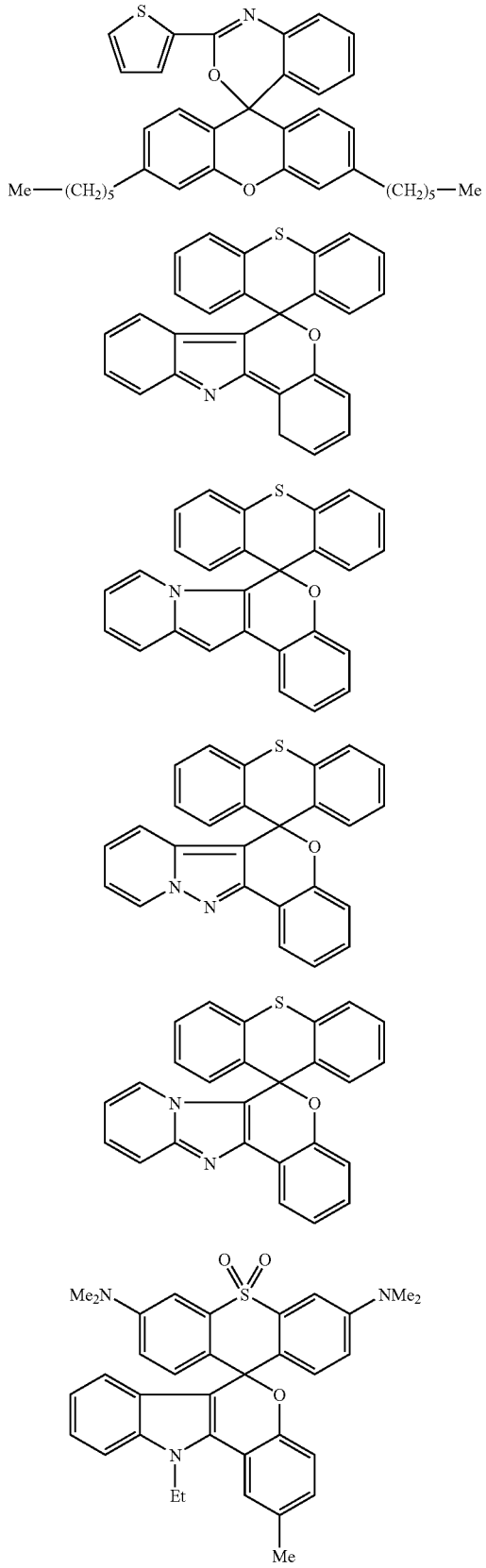
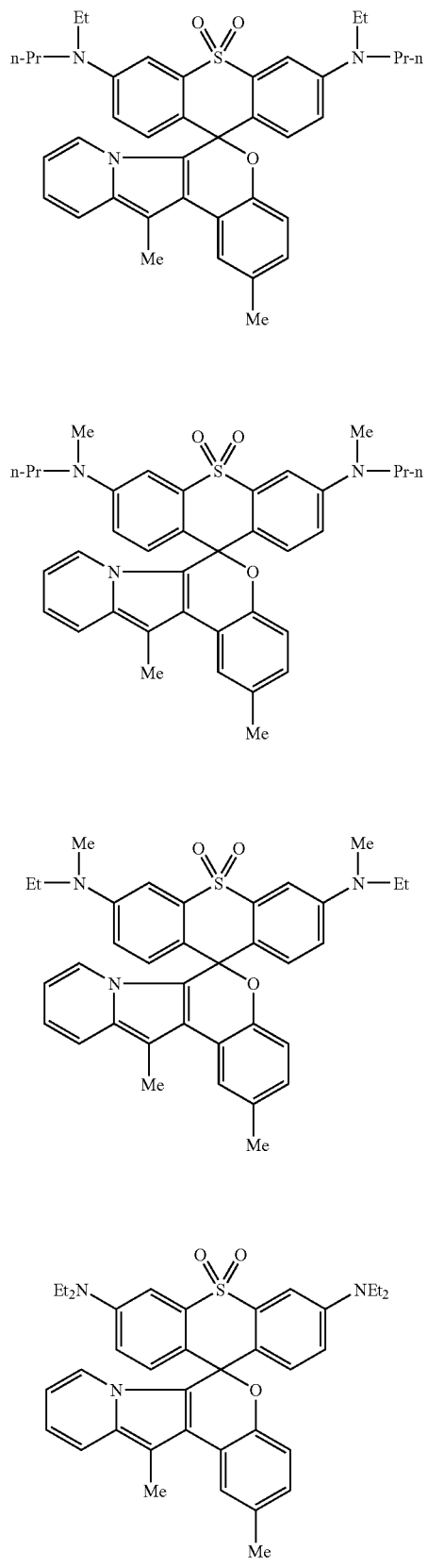

-continued
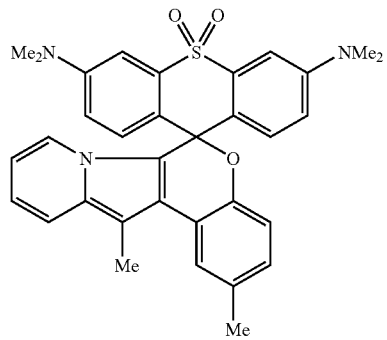
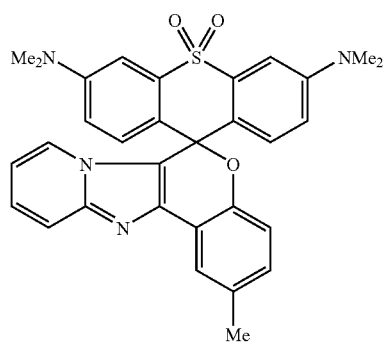
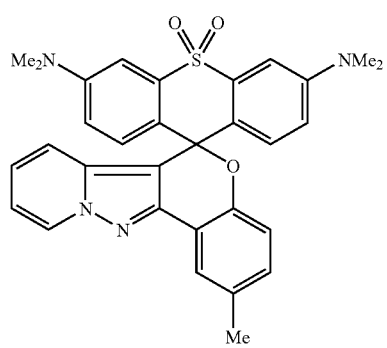
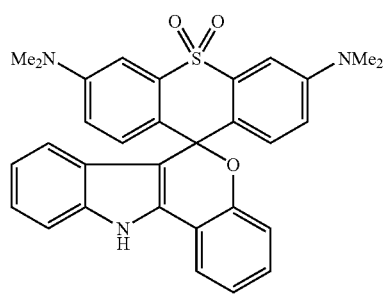
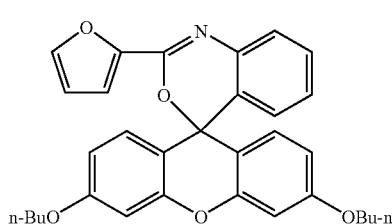
-continued
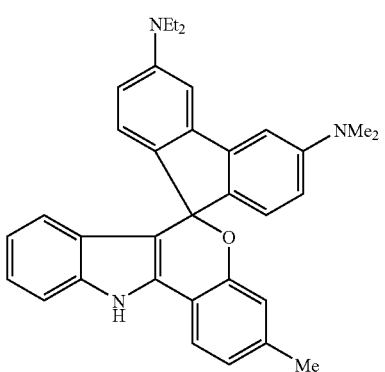
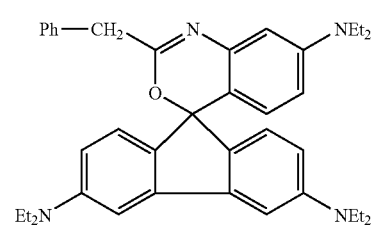
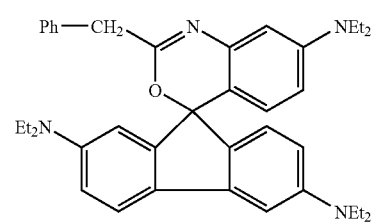
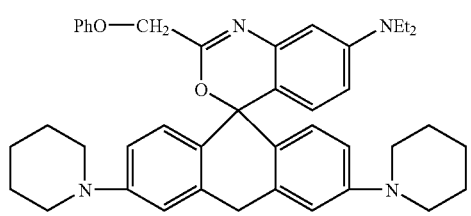
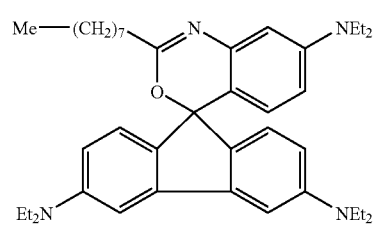
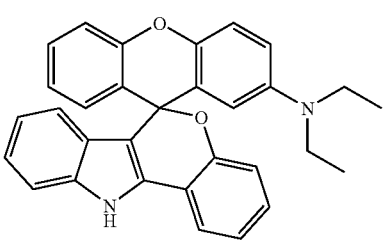

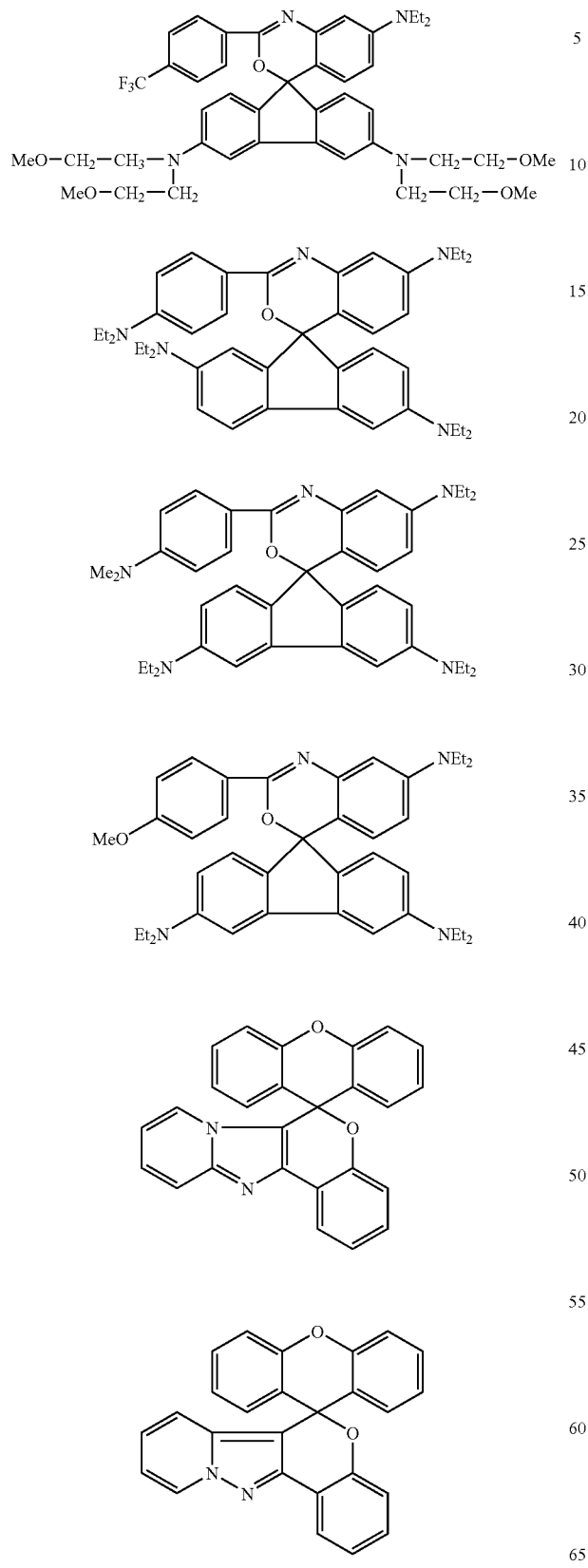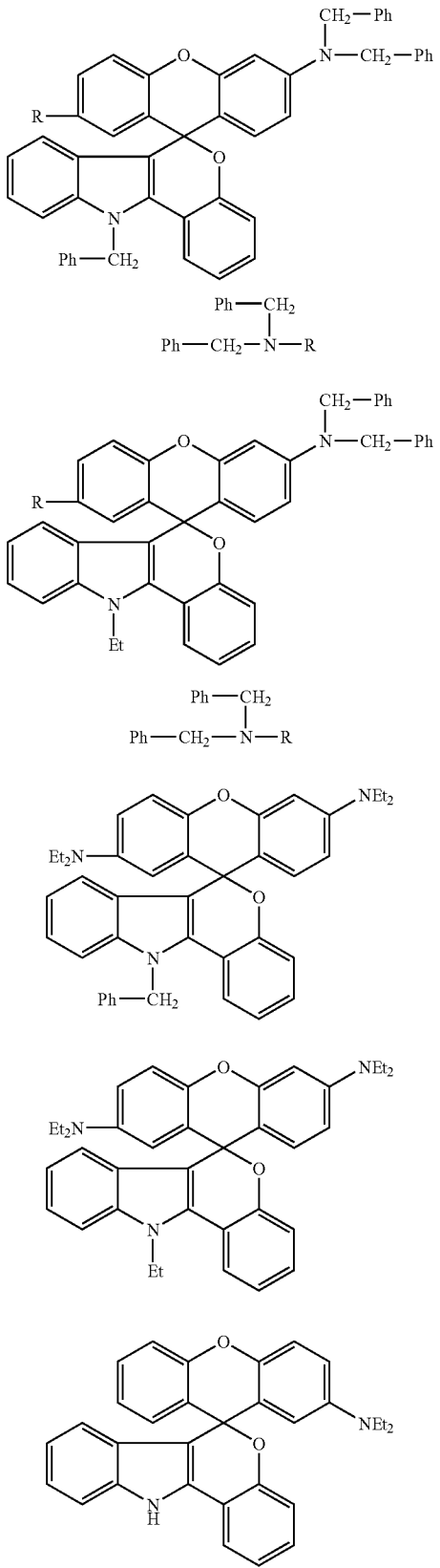

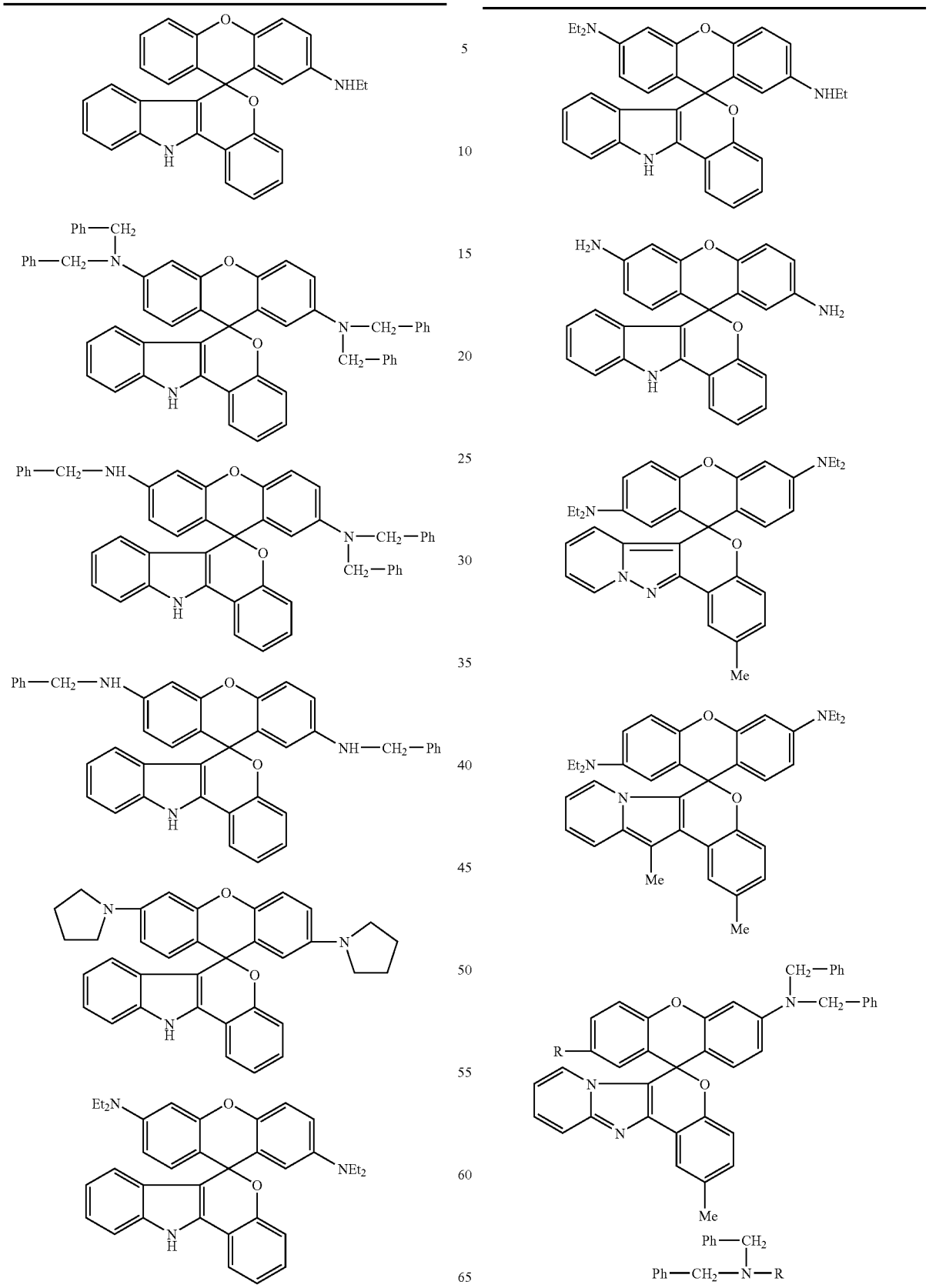

-continued
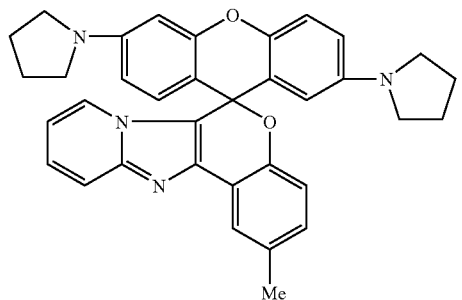
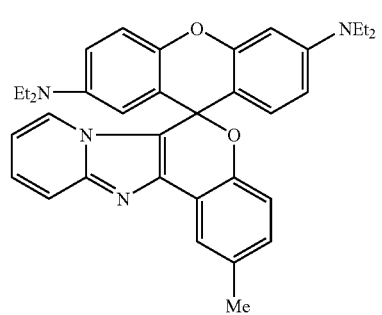
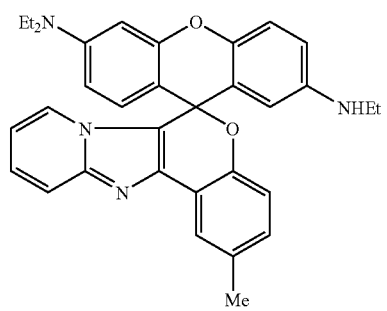
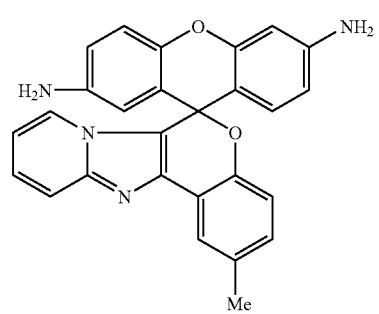
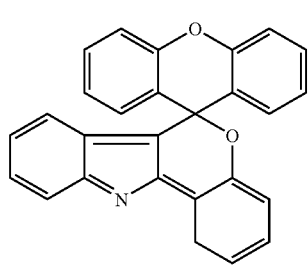
-continued
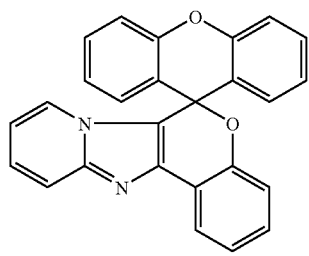
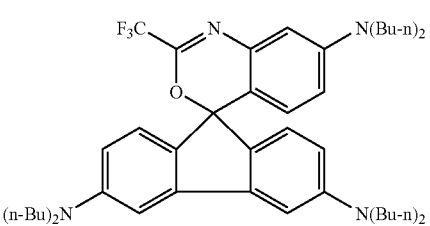
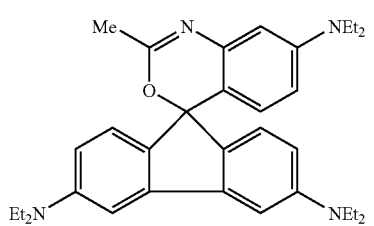
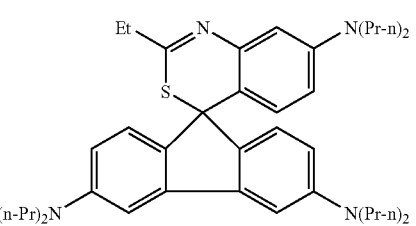
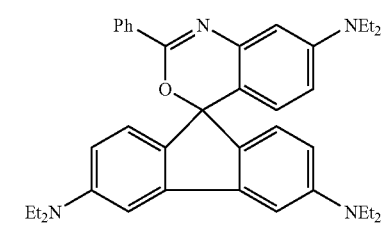
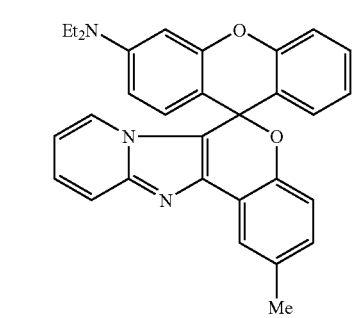

-continued
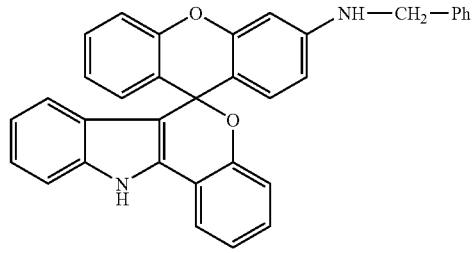
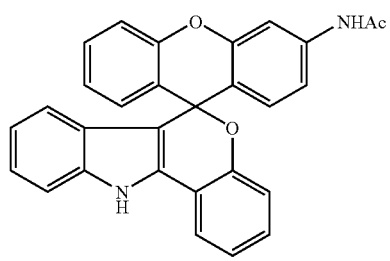
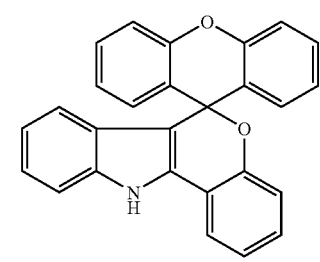
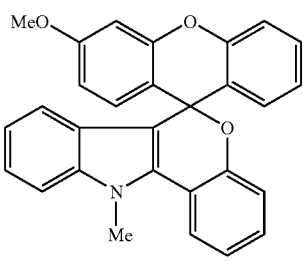
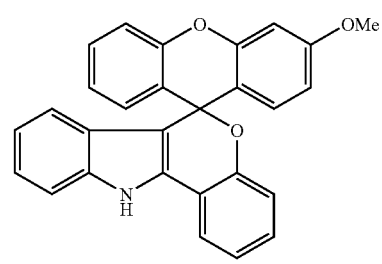
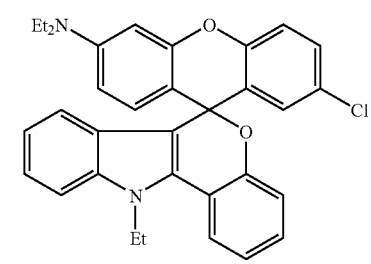
-continued
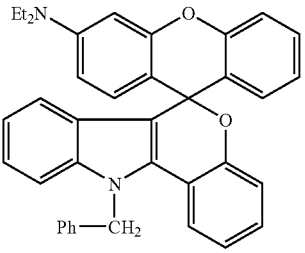
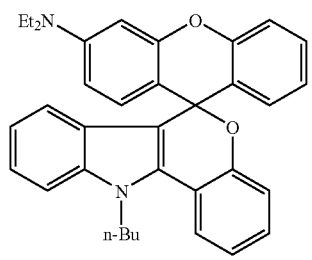
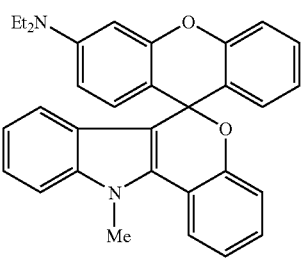
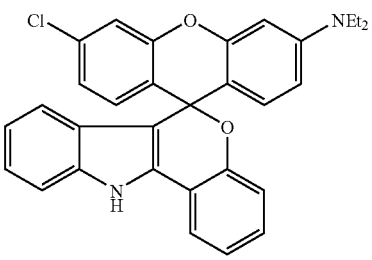
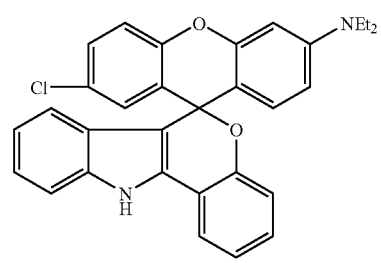
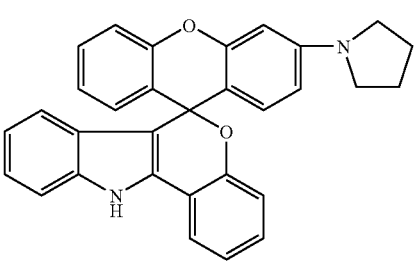

-continued
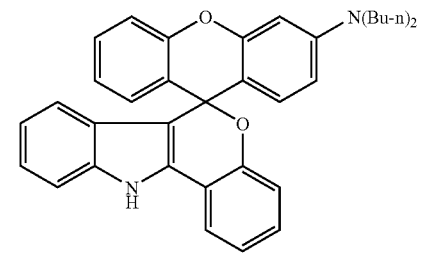
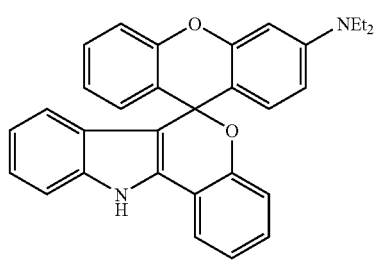
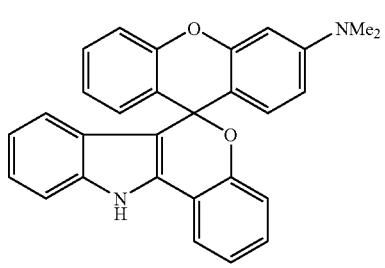
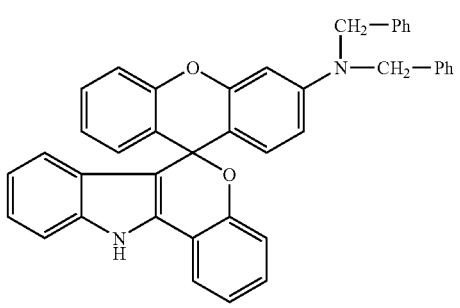
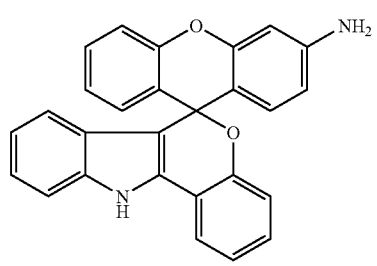
-continued
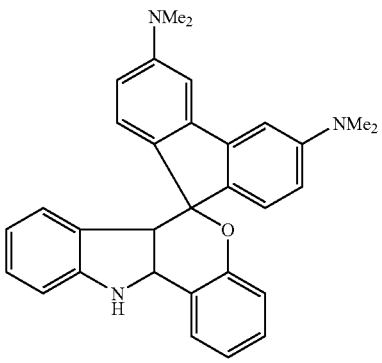
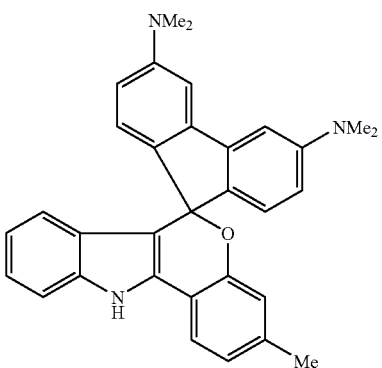
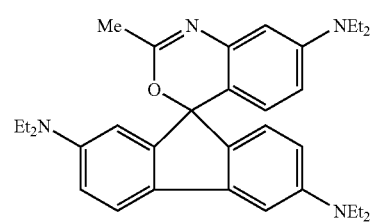
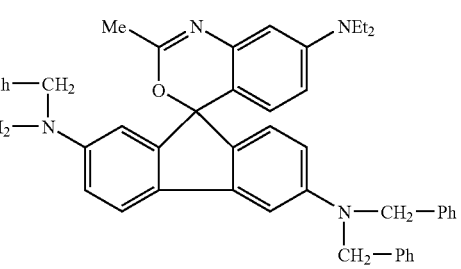
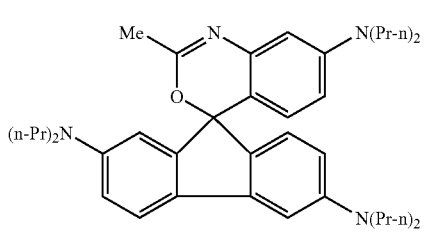

-continued
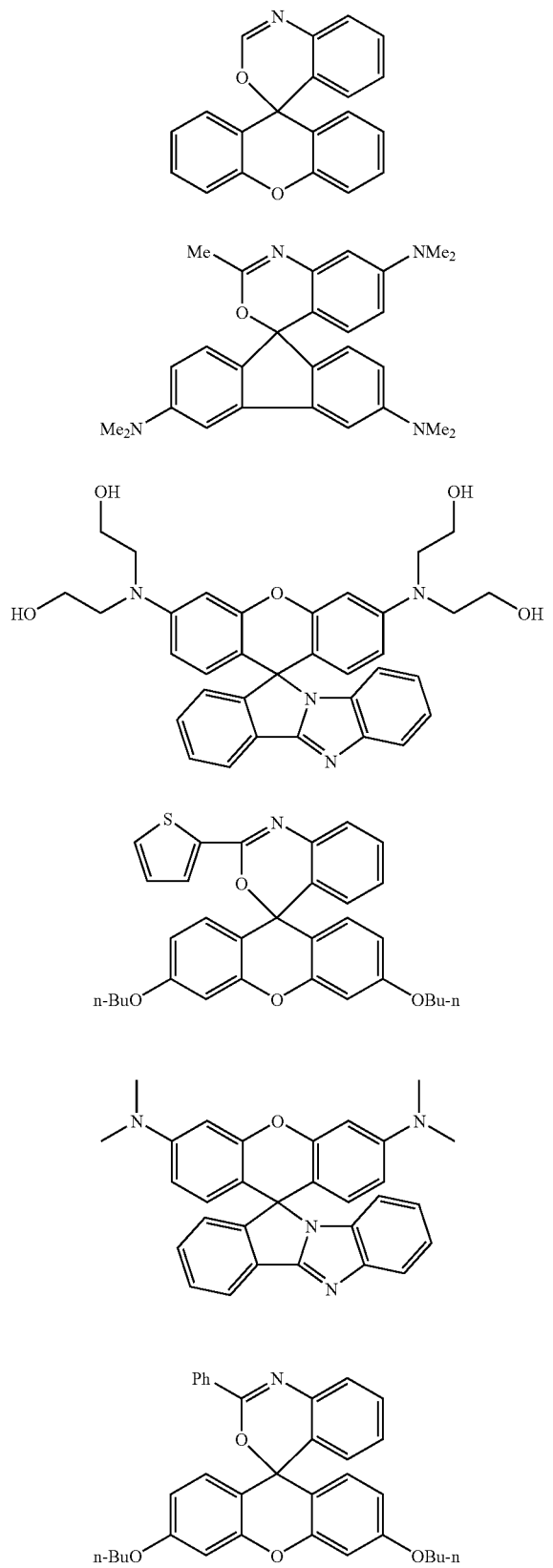
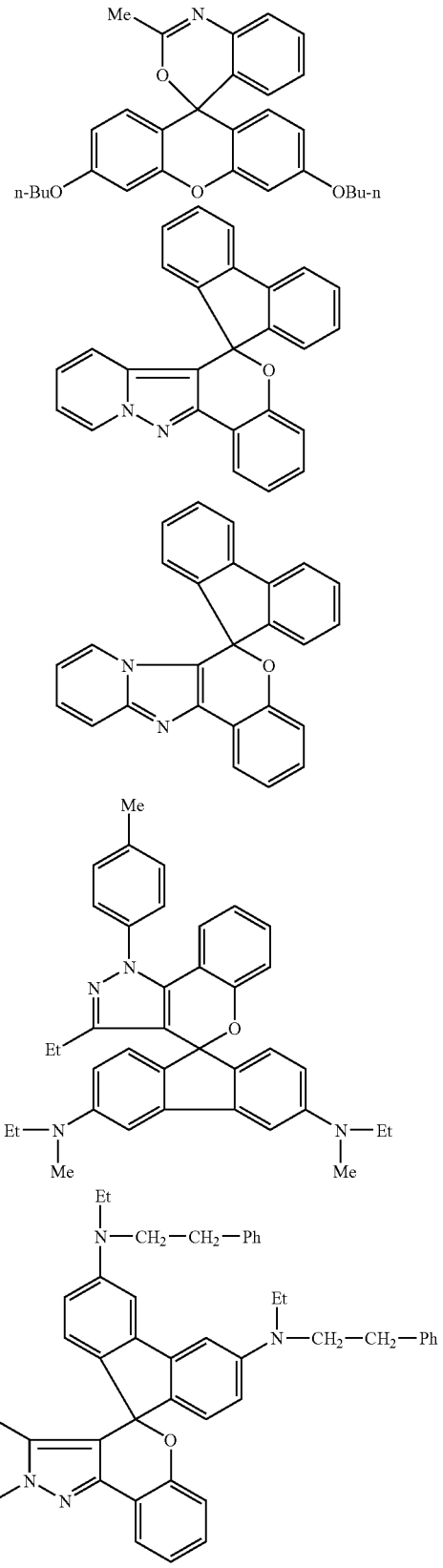

-continued
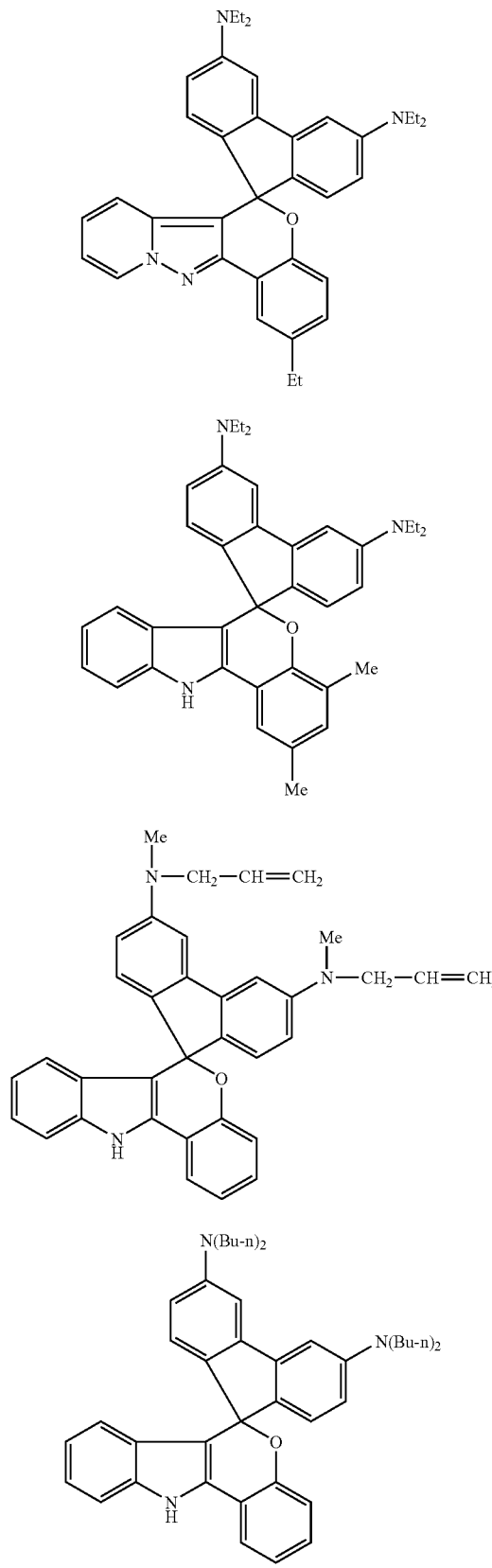
-continued
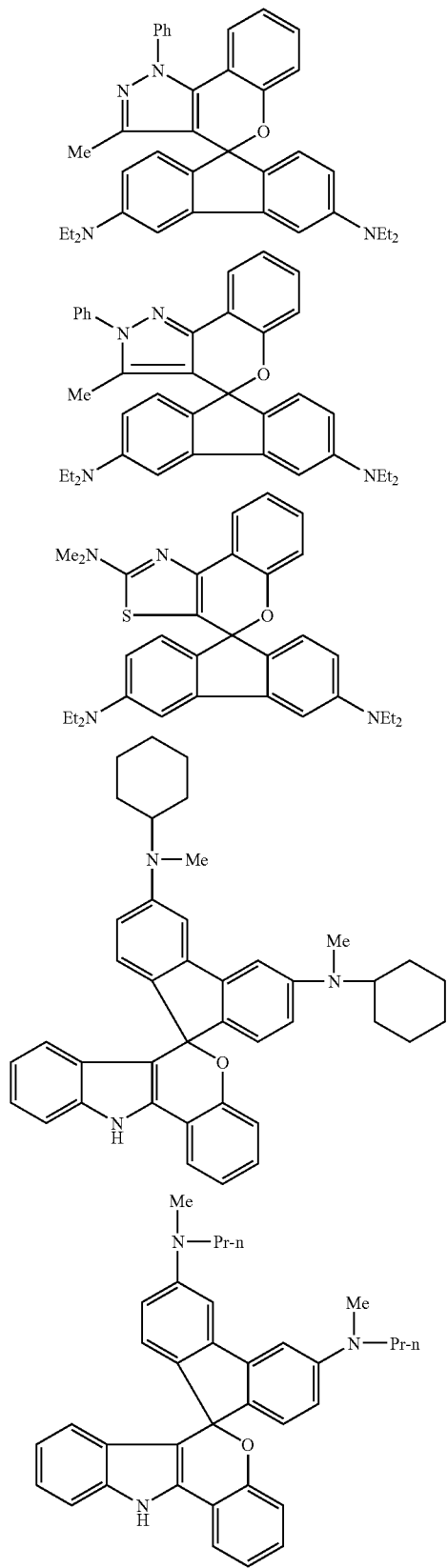

-continued
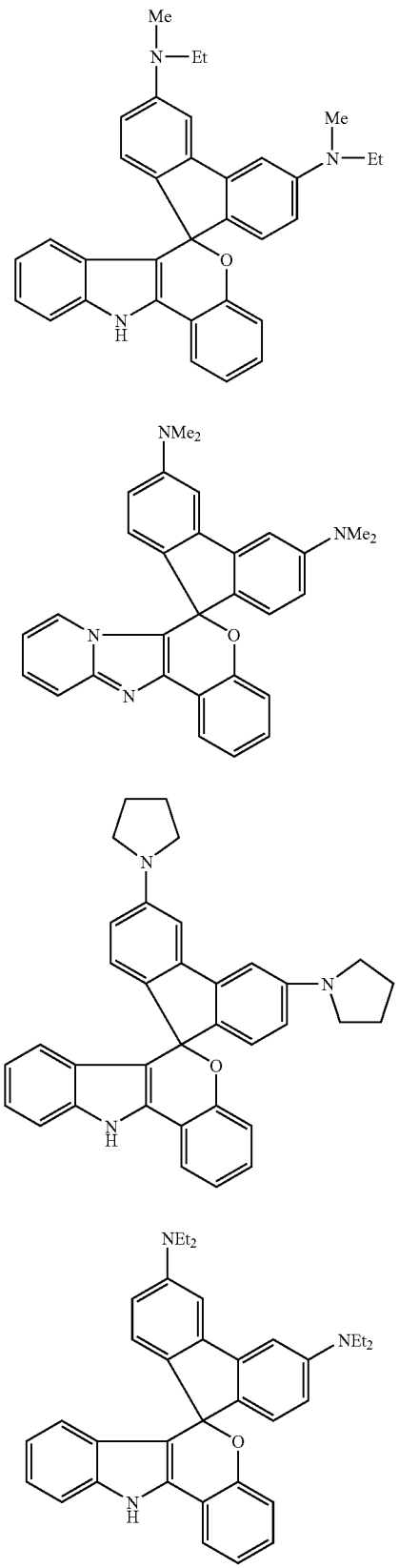
-continued
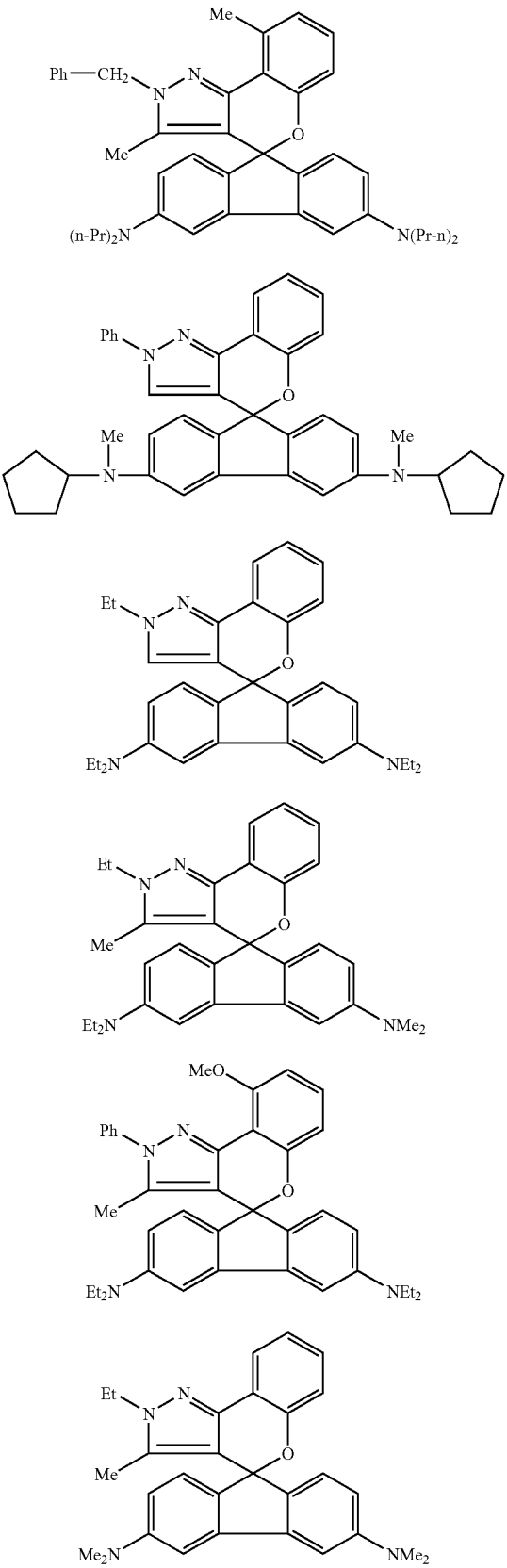

-continued
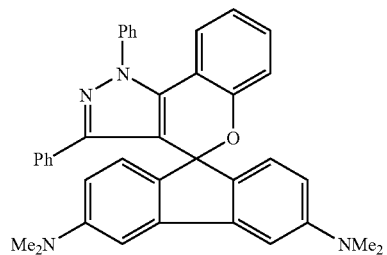
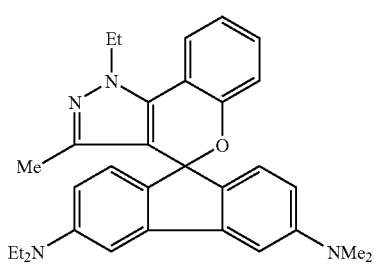
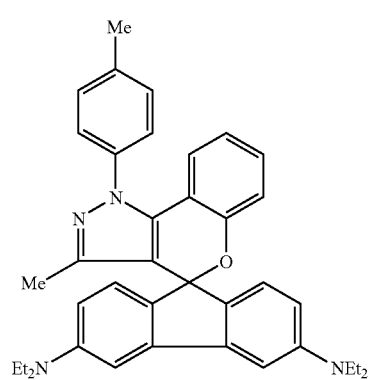
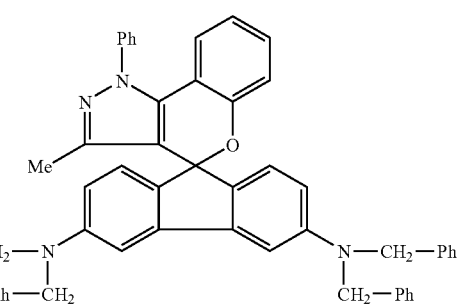
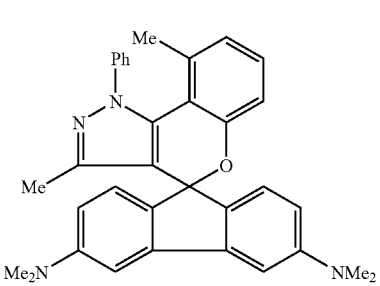
-continued
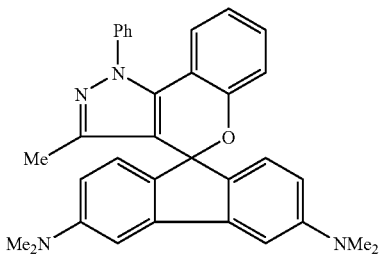
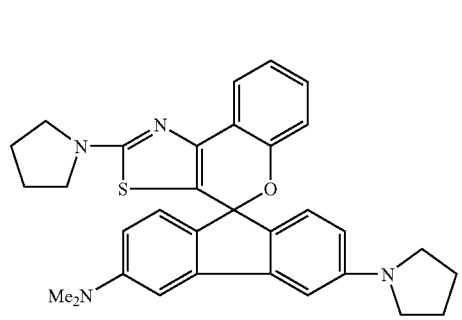
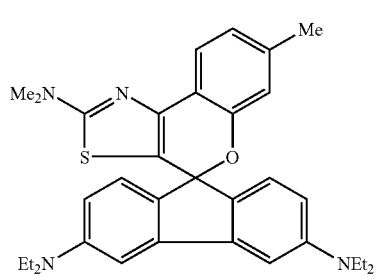
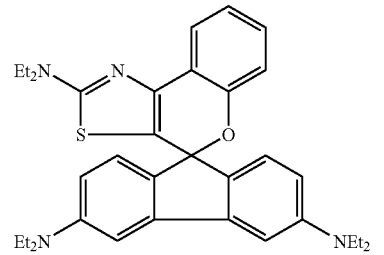
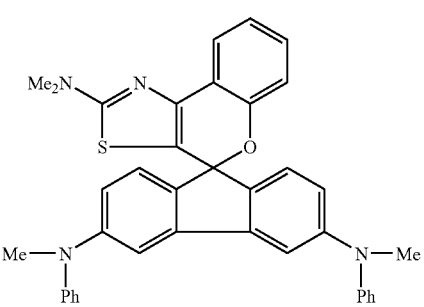

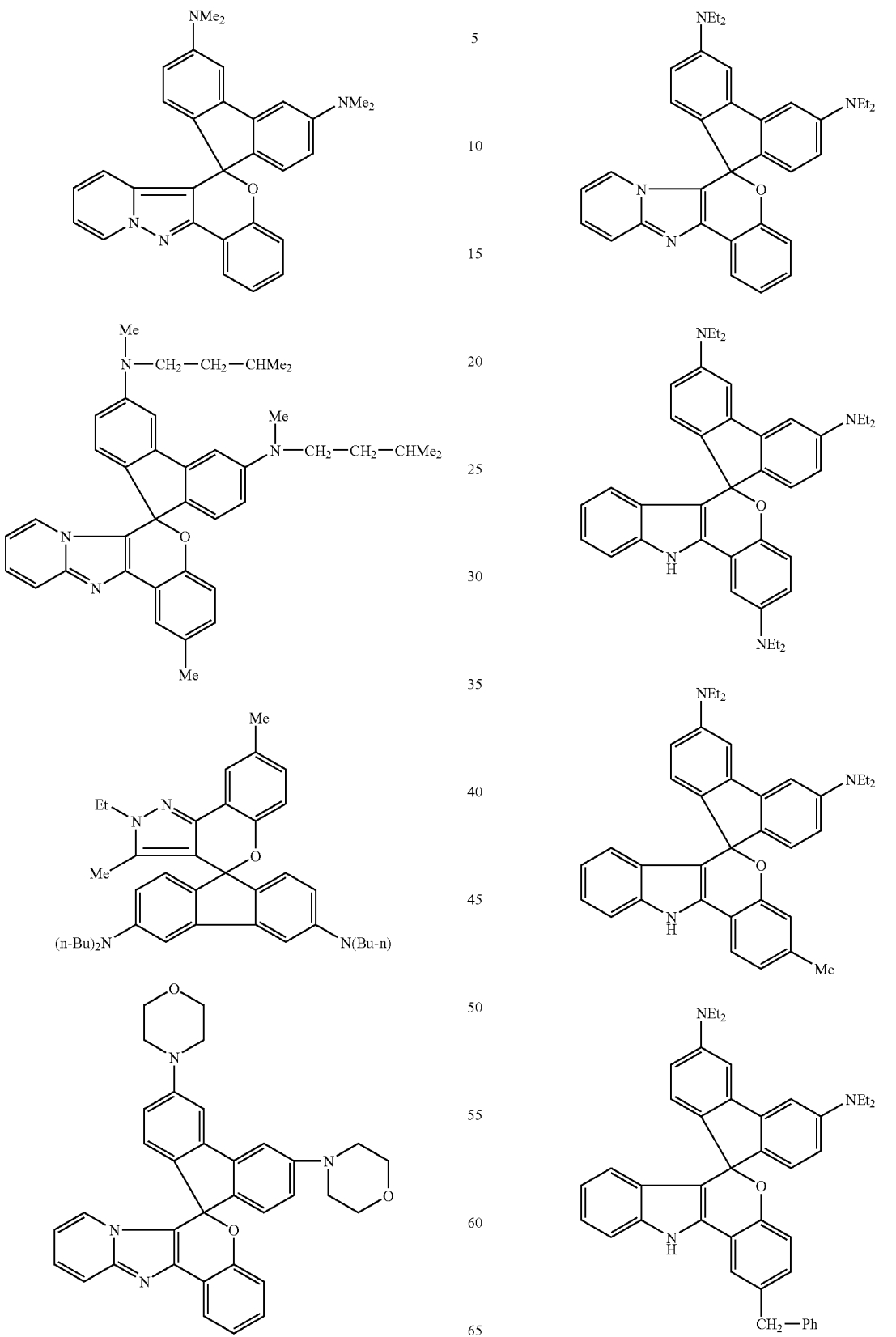

-continued
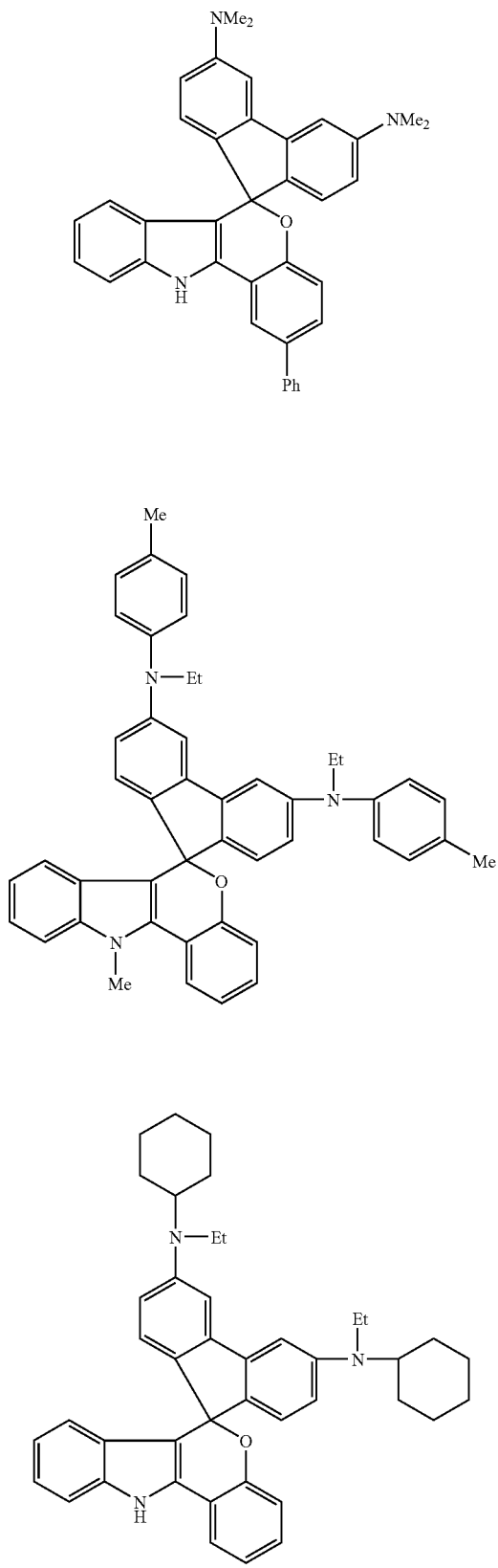
-continued
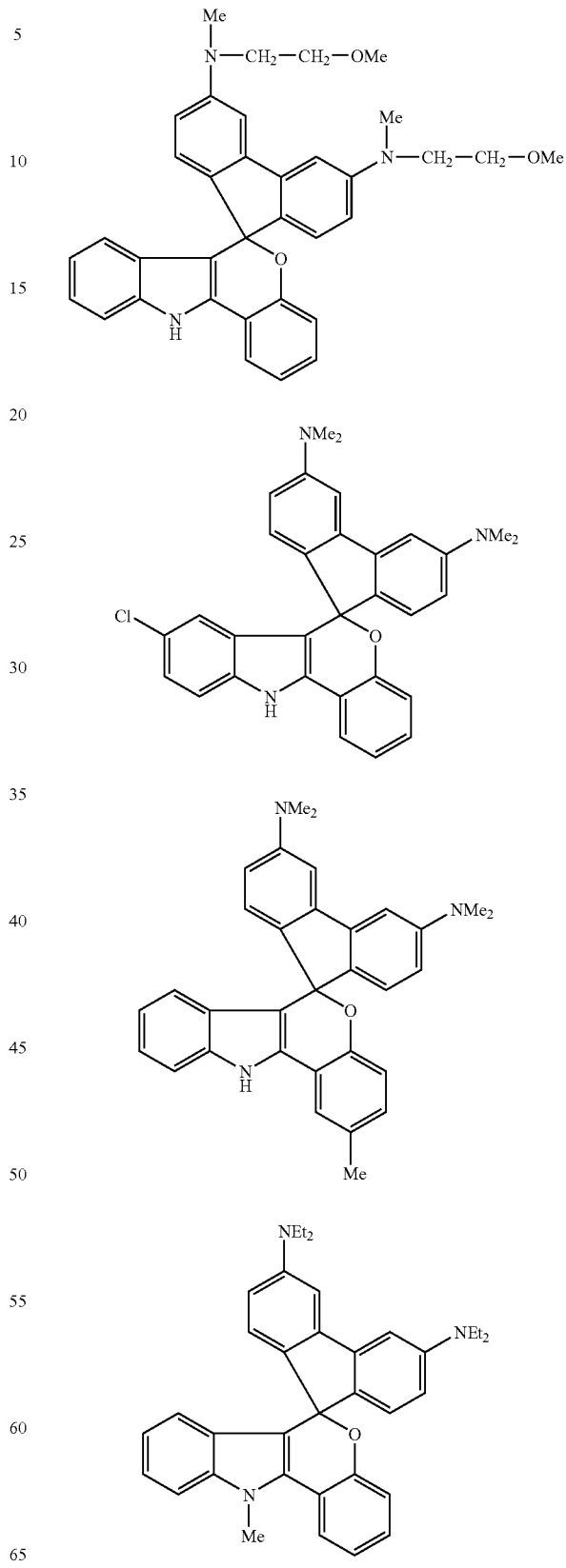

-continued
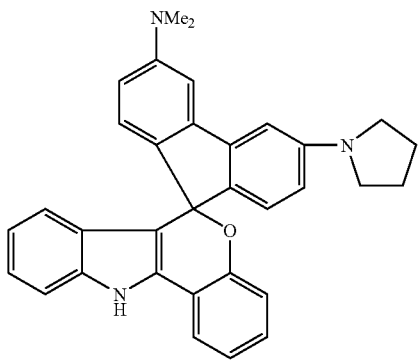
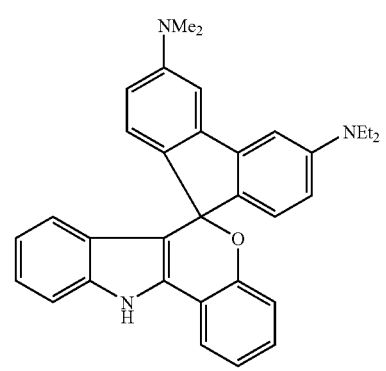
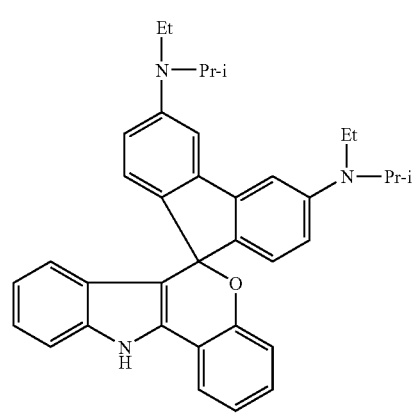
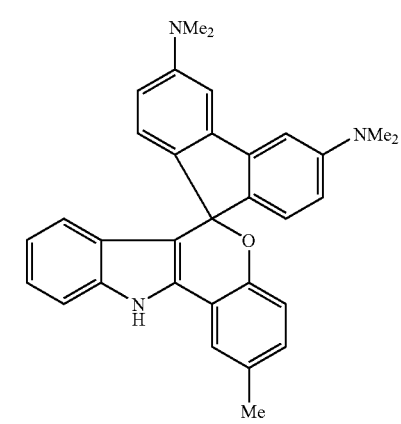
-continued
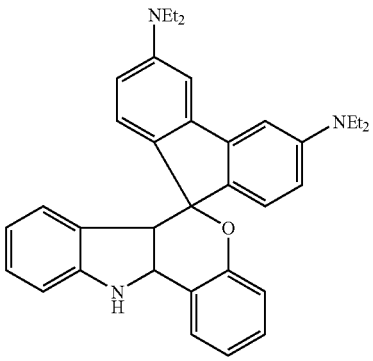
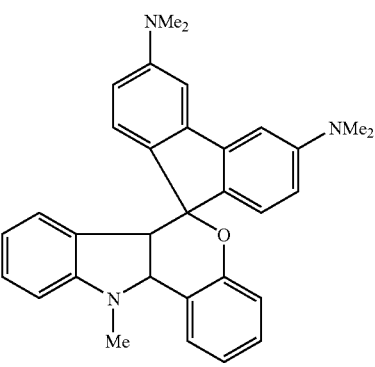
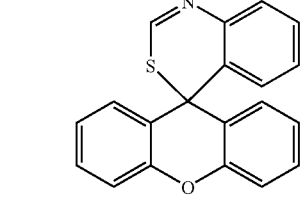
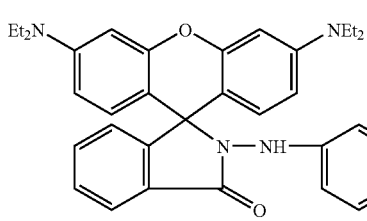
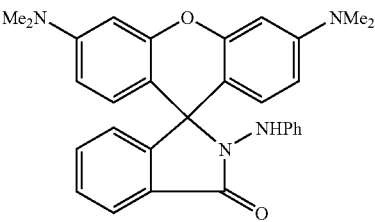

-continued
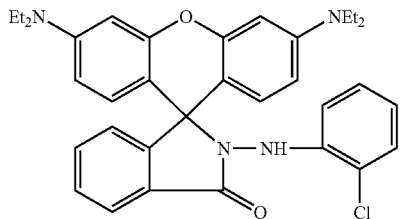
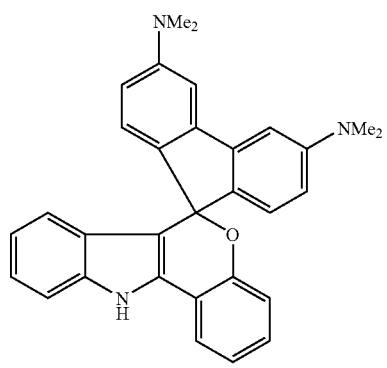
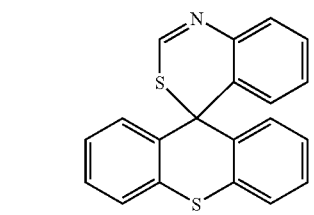
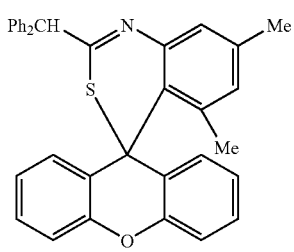
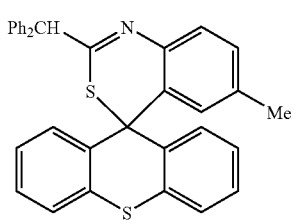
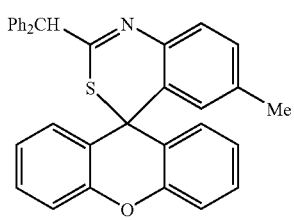
-continued
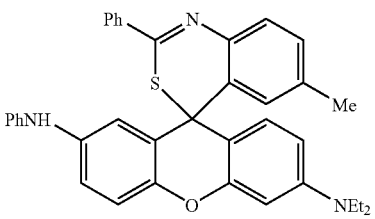
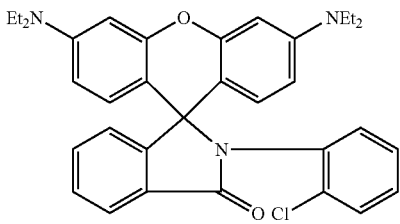
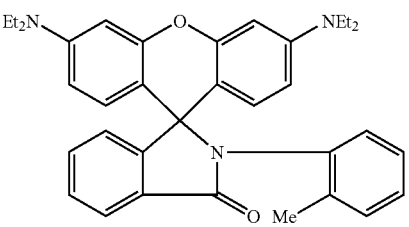
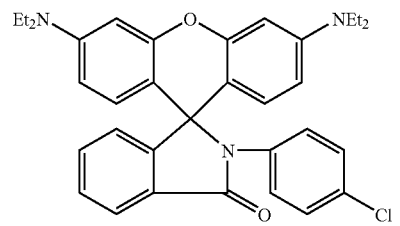
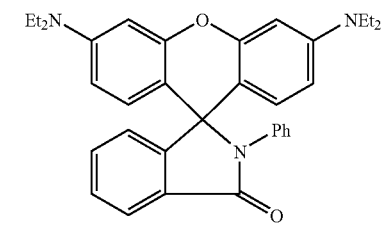
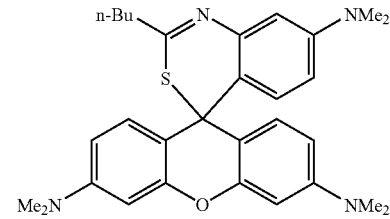

In at least one embodiment, the compounds of formula (I) are chosen from the following compounds:

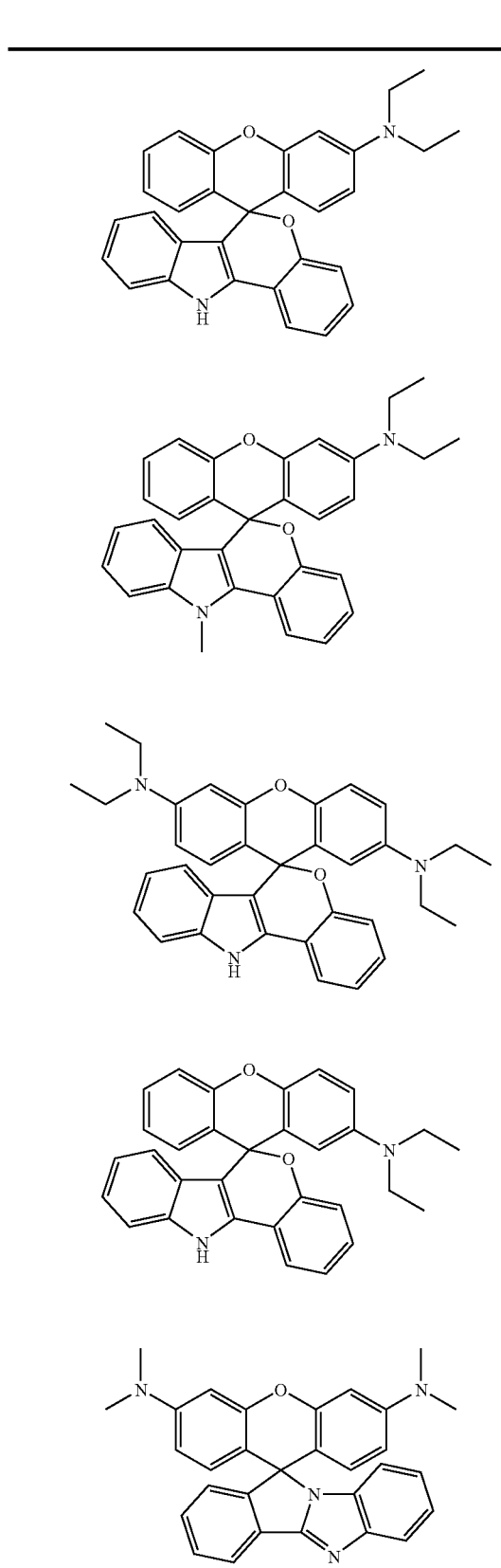

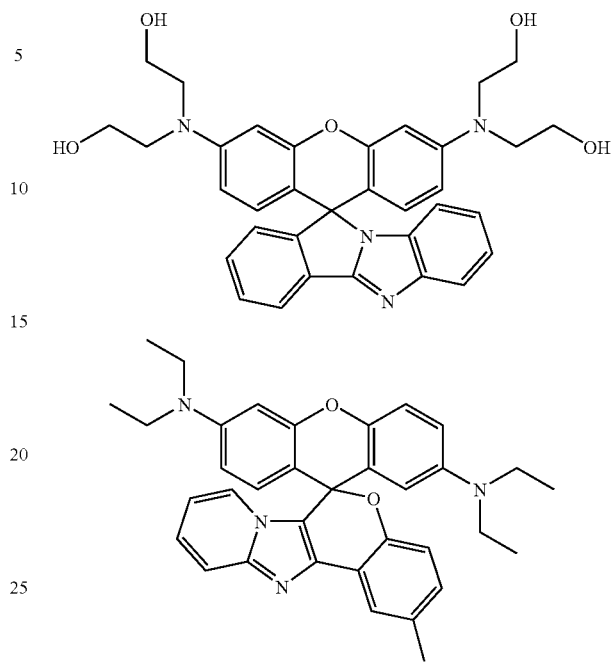

In one embodiment, the compounds chosen from the compounds of formula (I), the dyes corresponding to the compounds of formula (I) wherein the ring H is open, and the addition salts thereof are present in an amount ranging from 0.001 to 10% by weight, relative to the total weight of the dyeing composition, such as from 0.005 to 5% by weight.

In another embodiment, the addition salts of the compounds of formula (I) and of the dyes corresponding to the compounds of formula (I) wherein the ring H is open which can be used in the context of the disclosure are chosen from the acid addition salts thereof, such as hydrochlorides, hydrobromides, sulphates, methosulphates, gluconates, citrates, succinates, tartrates, lactates, tosylates, benzenesulphonates, phosphates and acetates, and the addition salts with a base, such as sodium hydroxide, potassium hydroxide, ammonia, amines and alkanolamines.

The composition in accordance with the disclosure can additionally comprise at least one direct dye, which can, for example, be chosen from nitrobenzene dyes, azo direct dyes, methine direct dyes and natural dyes. These direct dyes can be non-ionic, anionic or cationic in nature.

When at least one additional direct dye is present in the composition in accordance with the disclosure, it is generally present in an amount ranging from 0.001 to 20% by weight, relative to the total weight of the dyeing composition, such as from 0.01 to 10% by weight.

The composition of the present disclosure can additionally comprise at least one oxidation dye chosen from oxidation bases and couplers conventionally used in oxidation dyeing.

When at least one oxidation dye is present in the composition in accordance with the disclosure, it is generally present in an amount ranging from 0.001 to 20% by weight, relative to the total weight of the dyeing composition, such as from 0.01 to 10% by weight.

The medium appropriate for dyeing, also known as dyeing vehicle, is generally composed of water, or of at least one organic solvent, or of a mixture of water and of at least one organic solvent. Mention may be made, as organic solvent, for example, but not by way of limitation, of ketones, such as acetone; $C_1$-$C_4$ alkanols, such as ethanol and isopropanol; polyols, such as propylene glycol, glycerol and hexylene glycol; polyol ethers, such as 2-butoxyethanol, propylene glycol monomethyl ether, diethylene glycol monoethyl ether and diethylene glycol monomethyl ether; and mixtures thereof.

The at least one solvent is generally present in an amount ranging from 1 to 40% by weight, relative to the total weight of the dyeing composition, for example from 5 to 30% by weight.

The compounds chosen from the compounds of formula (I), the dyes corresponding to the compounds of formula (I) wherein the ring H is open, and the addition salts thereof are either soluble or in dispersion in the dyeing vehicle.

The composition in accordance with the disclosure can also include at least one adjuvant chosen from various adjuvants conventionally used in hair dyeing compositions, such as anionic, cationic, non-ionic, amphoteric or zwitterionic surfactants or their mixtures; anionic, cationic, non-ionic, amphoteric or zwitterionic polymers or their mixtures; inorganic or organic thickening agents, such as anionic, cationic or non-ionic and amphoteric polymeric associative thickeners; antioxidants; penetration agents; sequestering agents; fragrances; dispersing agents; conditioning agents, such as, for example, cationic or amphoteric polymers; cations; volatile or non-volatile and modified or unmodified silicones; chitosans or chitosan derivatives; film-forming agents; ceramides; preservatives or opacifying agents.

The above at least one adjuvant is generally present in an amount for each of them, ranging from 0.01 to 20% by weight, relative to the total weight of the composition.

Of course, a person skilled in the art will take care to choose this or these optional additional compounds so that the beneficial properties intrinsically attached to the dyeing composition in accordance with the disclosure are not, or not substantially, detrimentally affected by the envisaged addition or additions.

When the dyeing vehicle comprises water or a mixture of water and of at least one organic solvent, the pH of the dyeing composition in accordance with the disclosure ranges from 3 to 12, for example from 4 to 11 or from 6 to 8.5. It can be adjusted to the desired value via at least one acidifying or basifying agent commonly used in the dyeing of keratinous fibers or else using at least one conventional buffering system.

Non-limiting mention may be made, among acidifying agents, by way of example, of inorganic acids, such as, for example, hydrochloric acid, nitric acid or sulphuric acid, or organic acids, such as, for example, compounds comprising at least one carboxylic acid functional group, such as acetic acid, tartaric acid, citric acid or lactic acid, one sulphonic acid functional group, one phosphonic acid functional group or one phosphoric acid functional group.

Non-limiting mention may be made, among basifying agents, by way of example, of:

basic amino acids;

alkali metal or alkaline earth metal carbonates or bicarbonates;

silicates or metasilicates;

compounds of formula (II):

wherein:

X is chosen from potassium, lithium, sodium, ammonium $N^+R_{13}R_{14}R_{15}R_{16}$ ions with $R_{13}$, $R_{14}$, $R_{15}$ and $R_{16}$, which are identical or different, denoting a $C_2$-$C_4$ alkyl radical, when n is equal to 1;

X is chosen from magnesium or calcium atoms, when n is equal to 2;

compounds of formula (III):

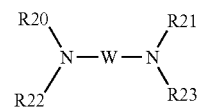

wherein:

$R_{17}$ is chosen from hydrogen atoms, $C_1$-$C_6$ alkyl radicals, $C_1$-$C_6$ monohydroxyalkyl radicals and $C_2$-$C_6$ polyhydroxyalkyl radicals;

$R_{18}$ and $R_{19}$, which are identical or different, are chosen from hydrogen atoms, $C_1$-$C_6$ alkyl radicals, $C_1$-$C_6$ monohydroxyalkyl radicals and $C_2$-$C_6$ polyhydroxyalkyl radicals;

compounds of formula (IV):

$$R_{20} \diagdown N - W - N \diagup R_{21}$$
$$R_{22} \diagup \qquad \diagdown R_{23}$$

wherein:

W is a propylene residue optionally substituted by a hydroxyl group or a $C_1$-$C_4$ alkyl radical;

$R_{20}$, $R_{21}$, $R_{22}$ and $R_{23}$, which are identical or different, are chosen from hydrogen atoms, $C_1$-$C_4$ alkyl radicals and $C_1$-$C_4$ hydroxyalkyl radicals.

As used herein, the term "basic amino acid" is understood to mean either (i) an amino acid exhibiting an additional cationic (or basic) group in addition to the amine functional group positioned in the a position with respect to the carboxyl group; or (ii) an amino acid exhibiting a cationic (or basic) (hydrophilic) side chain; or (iii) an amino acid carrying a side chain composed of a nitrogenous base. These definitions are generally known and published in general biochemical works, such as J. H. Weil (1983), pages 5 et seq., Lubert Stryer (1995), page 22, A. Lehninger (1993), pages 115-116, and De Boeck-Wesmael (1994), pages 57-59.

In at least one embodiment, the at least one basic amino acid in accordance with the disclosure is chosen from those of formula (D):

where $R_{24}$ denotes a group chosen from:

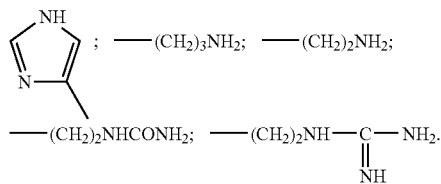

Non-limiting mention may be made, among the compounds of formula (D), by way of example, of histidine, lysine, ornithine, citrulline or arginine.

The composition according to the present disclosure can be provided in various forms, such as in the form of liquids, creams or gels or in any other form appropriate for dyeing keratinous fibers, such as human hair.

The method for treating keratinous fibers in accordance with the disclosure can make it possible to obtain an intense and persistent coloring, the highlights of which can vary according to the pH and the temperature, and which can be erased and reformed at least once without substantial loss of color. In one embodiment, the coloring is modified, erased or reformed by adjusting the pH using at least one acidifying agent or at least one basifying agent.

Within the meaning of the present disclosure, the coloring is "erased" when the keratinous fibers have returned to their original color. The coloring is "modified" when the coloring obtained is different from that obtained during the preceding stage. The coloring is "reformed" when the coloring obtained for the keratinous fibers is substantially the same as that which had been obtained during a preceding stage and which had subsequently been modified.

The coloring obtained depends on the compounds of formula (I) which are applied to the keratinous fibers. When all these compounds have their ring H opened, the coloring may be intense. By varying the pH or the temperature, it is possible to erase this coloring by changing from a situation where all the compounds of formula (I) have the ring H open to a situation where all the compounds of formula (I) have the ring H closed and then to reform it by changing from a situation where all the compounds of formula (I) have the ring H closed to a situation where all the compounds of formula (I) have the ring H open. It is also possible to vary the ratio of the concentration of compounds of formula (I) wherein the ring H is open to the concentration of compounds of formula (I) wherein the ring H is closed. The coloring is then modified in intensity or color according to whether at least one compound of formula (I) wherein the ring H is closed or at least one compound of formula (I) wherein the ring H is open is/are applied to the keratinous fibers and according to their relative sensitivity to pH or to temperature.

In at least one embodiment, the method for treating keratinous fibers, such as human keratinous fibers, such as the hair, comprises:

applying a dyeing composition according to the disclosure to the keratinous fibers for a sufficient development time, the pH being adjusted using at least one first acidifying agent or at least one first basifying agent according to the coloring desired; and optionally modifying the coloring of the keratinous fibers using at least one second acidifying agent or at least one second basifying agent applied to the keratinous fibers.

The application of the dyeing composition according to the disclosure may or may not be followed by a rinsing operation.

According to one embodiment of the disclosure, the at least one acidifying agent or the at least one basifying agent is mixed with the dyeing composition before application to the keratinous fibers.

According to another embodiment of the disclosure, the at least one acidifying agent or the at least one basifying agent is applied before or after the dyeing composition. It is possible to have a gap of 5 to 30 minutes between the application of the at least one acidifying agent or at least one basifying agent and the application of the dyeing composition. In at least one embodiment, the at least one acidifying agent or the at least one basifying agent is applied after the dyeing composition.

The development time of the composition in accordance with the disclosure generally ranges from 3 to 60 minutes, for example from 5 to 40 minutes or from 10 to 20 minutes.

The application temperature generally ranges from ambient temperature to 80° C., for example from 25 to 55° C.

The keratinous fibers may or may not be rinsed after application of the at least one acidifying agent or at least one basifying agent.

The at least one acidifying or basifying agent is chosen from those which are described above.

Another aspect of the present disclosure is a multi-compartment device or kit which makes it possible to carry out the method for coloring keratinous fibers described above.

The multi-compartment kit of the present disclosure comprises, in at least one first compartment, at least one composition in accordance with the disclosure and, in at least one second compartment, at least one acidifying agent or at least one basifying agent. In one embodiment, the multi-compartment kit of the disclosure comprises, in the at least one second compartment, at least one acidifying agent and, in at least one third compartment, at least one basifying agent.

Also disclosed herein is a composition for dyeing keratinous fibers, such as human keratinous fibers, such as the hair, as defined above and additionally comprising at least one surfactant and at least one polymer, for example an associative or non-associative thickening polymer.

The at least one surfactant can be chosen from anionic, cationic, non-ionic, amphoteric and zwitterionic surfactants.

As used herein, "associative polymer" is understood to mean any polymer comprising at least one $C_8$-$C_{30}$ fatty chain.

As used herein, "thickening polymer" is understood to mean any polymer which, introduced into the polymer-free composition at 25° C., makes it possible to increase the viscosity thereof, for example any polymer which, introduced into the polymer-free composition at 1% of active material, makes it possible to increase the viscosity thereof by at least 100 cPs at a temperature of 25° C. and at a shear rate of 1 s$^{-1}$. This viscosity can be measured, for example, using a viscosimeter of cone/plate type.

Non-limiting mention may be made, as examples of associative thickening polymers, of associative polyurethane derivatives, associative cellulose derivatives, associative polyvinyllactam derivatives and associative poly(unsaturated acid) derivatives.

Non-limiting mention may be made, as examples of non-associative thickening polymers, of crosslinked acrylic acid homopolymers; crosslinked homopolymers of 2-acrylamido-2-methylpropanesulphonic acid and their crosslinked copolymers with acrylamide, partially or completely neutralized; homopolymers of ammonium acrylate or copolymers of ammonium acrylate and of acrylamide; homopolymers of dimethylaminoethyl methacrylate quaternized with methyl chloride or copolymers of dimethylaminoethyl methacrylate quaternized with methyl chloride and of acrylamide; non-ionic guar gums; biopolysaccharide gums of microbial origin, such as scleroglucan gum or xanthan gum; gums resulting from plant exudates, such as gum arabic, gum ghatti, gum karaya and gum tragacanth; hydroxypropyl or carboxymethyl celluloses; pectins; and alginates.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

By way of non-limiting illustration, a concrete example of certain embodiments of the present disclosure is given below.

EXAMPLE

Dye

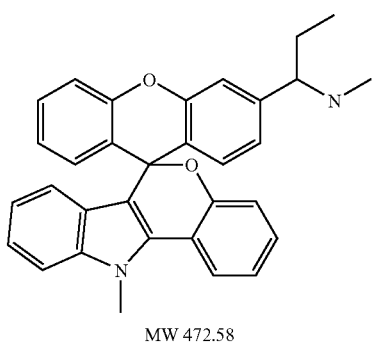

MW 472.58

Composition According to the Disclosure:

|  | Composition |
| --- | --- |
| Dye | 2 g |
| Benzyl alcohol | 4 g |
| Polyethylene glycol 6 EO | 6 g |
| Methanesulphonic acid | q.s. for pH 3 |
| Demineralized water | q.s. for 100 g |

This composition was applied to locks of grey hair comprising 90% of natural and permed white hairs, in a proportion of 5 g per 1 g of hair, at ambient temperature for 30 minutes. At the end of the development time, the lock was dried.

The hair coloring was evaluated visually. The shade obtained was a dark purple.

The locks thus colored had their coloring removed very rapidly by application of a 0.1M sodium hydroxide solution. The locks regained their original shade.

What is claimed is:

1. A composition for the coloring of human keratinous fibers comprising, in a medium appropriate for dyeing comprising water and/or at least one organic solvent, at least one compound chosen from the compounds of formula (I) comprising a cyclic group G including a ring H capable of opening, the dyes corresponding to the compounds of formula (I) wherein the ring H is open, and the addition salts thereof

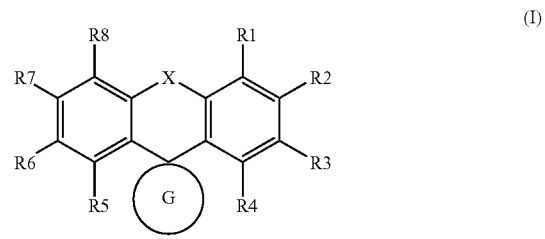

wherein:
$R_1$, $R_2$, $R_3$, $R_4$, $R_5$, $R_6$, $R_7$ and $R_8$ are chosen from, independently of one another:
hydrogen atoms
halo radicals;
hydroxyl radicals;
nitro radicals;
amino radicals;
carboxyl radicals;
aminocarbonyl radicals;
cyano radicals; and
radicals resulting from a hydrocarbon chain comprising from 1 to 100 carbon atoms, wherein the hydrocarbon chain is linear or branched, acyclic or mono- or polycyclic, fused or unfused, saturated or unsaturated, aromatic or nonaromatic, and optionally interrupted by at least one heteroatom chosen from nitrogen, oxygen and sulphur atoms or by at least one carbonyl group, which can be terminated by a hydrocarbonyl group or by a group comprising at least one heteroatom chosen from nitrogen, oxygen and sulphur atoms, which begins with a carbonyl group or with a group comprising at least one heteroatom chosen from nitrogen, oxygen and sulphur atoms, and which can be substituted by at least one group chosen from the following radicals: hydroxyl, halo, carboxyl, carboxy($C_1$-$C_9$)alkyl, cyano, amino and $C_1$-$C_6$ alkoxy;
it being possible for at least two of the $R_1$, $R_2$, $R_3$, $R_4$, $R_5$, $R_6$, $R_7$ and $R_8$ radicals carried by two adjacent carbon atoms to form, together and with the carbon atoms to which they are attached, at least one fused or unfused, aromatic, mono- or polycarbocyclic group comprising from 5 to 20 ring members, it being possible for at least one carbon atom to be replaced by an oxygen, nitrogen, sulphur or phosphorus atom, the aromatic mono- or polycarbocyclic group being unsubstituted or substituted by at least one radical chosen from a halo, hydroxyl, amino, carboxyl or $C_6$-$C_{18}$ aryl and cyano radicals;
the amino radicals being unsubstituted or substituted by one or two identical or different radicals chosen from $C_1$-$C_9$ alkyl radicals; $C_1$-$C_9$ hydroxyalkyl radicals;

$C_2$-$C_9$ alkenyl radicals; $C_6$-$C_{12}$ cycloalkyl radicals; $C_6$-$C_{18}$ aryl radicals optionally substituted by at least one radical chosen from halo or $C_1$-$C_9$ alkyl radicals; ($C_6$-$C_{18}$)arylcarbonyl radicals; cyclo($C_6$-$C_{12}$)alkyl($C_1$-$C_9$)alkyl radicals; ($C_6$-$C_{18}$)aryl($C_1$-$C_9$)alkyl radicals; ($C_1$-$C_9$)alkylcarbonyl radicals; ($C_1$-$C_9$)alkoxycarbonyl ($C_1$-$C_9$)alkyl radicals; α-naphthylalkyl radicals; $C_1$-$C_9$ haloalkyl radicals; $C_1$-$C_9$ cyanoalkyl radicals; $C_2$-$C_{15}$ acyl radicals; ($C_1$-$C_9$)alkoxycarbonyl radicals; ($C_6$-$C_{18}$) aryloxycarbonyl radicals; ($C_6$-$C_{18}$)aryloxy($C_1$-$C_9$)alkylcarbonyl radicals; ($C_6$-$C_{18}$)aryl($C_1$-$C_9$)alkoxycarbonyl radicals; ($C_1$-$C_9$)alkoxy($C_6$-$C_{18}$)arylcarbonyl radicals; ($C_1$-$C_9$)alkoxy($C_1$-$C_9$)alkylcarbonyl radicals; di($C_1$-$C_9$) alkylaminocarbonyl radicals; di($C_1$-$C_9$)alkylaminosulphonyl radicals; ($C_1$-$C_9$)alkyl($C_6$-$C_{18}$)arylsulphonyl radicals; ($C_1$-$C_9$)alkylsulphonyl radicals; di($C_1$-$C_9$) alkylamino($C_1$-$C_9$)alkyl radicals; and ($C_1$-$C_9$)alkoxy ($C_1$-$C_9$)alkyl radicals;

it being possible, when the amino radicals are substituted by two radicals, for the latter to form, with the nitrogen atom of the amino radical, a 5- or 6-membered heterocycle optionally comprising at least one additional heteroatom;

X represents a direct bond or a divalent atom, or a sulphone $SO_2$ or $C(R_{13})_2$ or $NR_{13}$ group;

G represents a divalent radical chosen from the formulae G1 to G7:

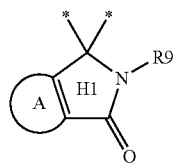

G1

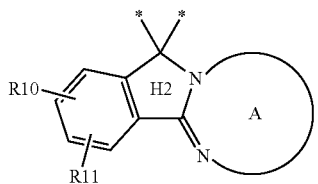

G2

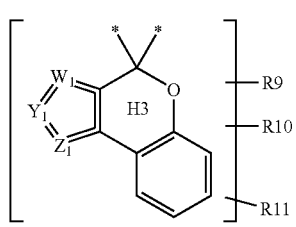

G3

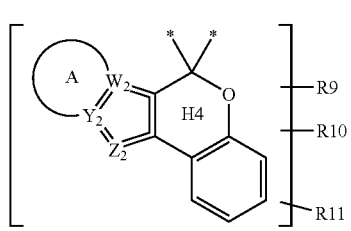

G4

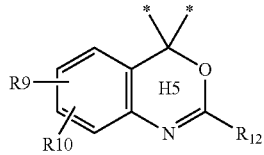

G5

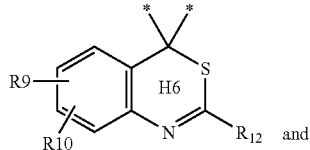

G6 and

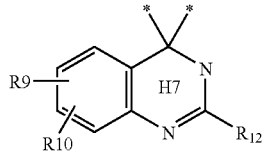

G7 wherein:

$Y_1$, $W_1$ and $Z_1$, on the one hand, and $Y_2$, $W_2$ and $Z_2$, on the other hand, are chosen from, independently of one another, carbon atoms, nitrogen atoms, sulphur atoms and divalent groups $CR_{13}$ and $NR_{13}$;

$R_9$, $R_{10}$, $R_{11}$ and $R_{13}$ have the same definitions as $R_1$;

$R_{12}$ is chosen from:
hydrogen atoms
$C_1$-$C_9$ alkyl radicals;
amino radicals;
$C_1$-$C_9$ alkoxy radicals;
$C_6$-$C_{18}$ aryl radicals, which are unsubstituted or substituted by at least one group chosen from hydroxyl radicals, $C_1$-$C_9$ alkyl radicals, $C_6$-$C_{18}$ aryl radicals, $C_6$-$C_{18}$ aryloxy radicals, $C_1$-$C_9$ alkoxy radicals, halo radicals, carboxyl radicals, cyano radicals and amino radicals which are substituted or unsubstituted;
furanyl radicals;
($C_1$-$C_9$)alkylthio radicals;
thienyl radicals;
phenylcarbonyl radicals;
trifluoroalkyl radicals; and
di($C_6$-$C_{18}$)aryl($C_1$-$C_9$)alkyl radicals; and A represents a $C_6$-$C_{18}$ aryl group or a heterocyclic group which is saturated or unsaturated, substituted or unsubstituted, comprising from 5 to 12 ring members; and the composition is appropriate for coloring human keratinous fibers; and wherein the pH of the composition ranges from 3 to 12.

2. The composition according to claim 1, wherein:

$R_1$, $R_4$, $R_5$ and $R_8$ denote hydrogen atoms;

$R_2$ and $R_7$ are chosen from, independently of one another, hydrogen atoms; halo radicals; $C_1$-$C_9$ alkyl radicals; $C_1$-$C_9$ alkoxy radicals; and substituted and unsubstituted amino radicals;

$R_3$ and $R_6$ are chosen from, independently of one another, hydrogen atoms; halo radicals; $C_1$-$C_9$ alkyl radicals; and substituted and unsubstituted amino radicals;

X is a direct bond, or is chosen from sulphur and oxygen atoms and $SO_2$ groups; and G is chosen from divalent radicals of formulae G1, G2, G3, G4, G5 and G6.

3. The composition according to claim 1, wherein G is a G1 group; X is an oxygen atom; $R_1$, $R_3$, $R_4$, $R_5$, $R_6$ and $R_8$ denote hydrogen atoms; $R_2$ and $R_7$ denote, independently of one another, substituted and unsubstituted amino radicals; $R_9$ is chosen from substituted and unsubstituted aryl radicals, and substituted and unsubstituted amino radicals; and A is chosen from substituted and unsubstituted benzene rings.

4. The composition according to claim 1, wherein G is a G2 group; X is an oxygen atom; $R_1$, $R_3$, $R_4$, $R_5$, $R_6$, $R_8$, $R_{10}$ and $R_{11}$ denote hydrogen atoms; $R_2$ and $R_7$ denote, independently of one another, substituted and unsubstituted amino radicals; and A is chosen from substituted and unsubstituted benzene rings.

5. The composition according to claim 1, wherein G is a G3 group; $R_1$, $R_3$, $R_4$, $R_5$, $R_6$, $R_8$, $R_{10}$ and $R_{11}$ denote hydrogen atoms; $R_2$ and $R_7$ are chosen from, independently of one another, hydrogen atoms and substituted and unsubstituted amino groups; $R_9$ is chosen from hydrogen atoms, substituted and unsubstituted alkyl groups, and alkoxy groups; X represents a direct bond; $W_1$ is chosen from sulphur atoms, carbon atoms substituted by hydrogen atoms, $C_1$-$C_4$ alkyl radicals, phenyl radicals, and amino groups carrying two $C_1$-$C_4$ alkyl groups, the two radicals optionally forming, with the nitrogen atom carrying them, a saturated 5-membered heterocycle; $Y_1$ is chosen from carbon atoms substituted by a hydrogen atom, $C_1$-$C_4$ alkyl radicals, phenyl radicals, amino groups carrying two $C_1$-$C_4$ alkyl groups, the two radicals optionally forming, with the nitrogen atom carrying them, a saturated 5-membered heterocycle, nitrogen atoms, $C_1$-$C_2$ alkyl radicals, phenyl radicals, and phenylalkyl groups, the alkyl group of which is a $C_1$-$C_4$ alkyl group; and $Z_1$ is chosen from nitrogen atoms, NH groups, nitrogen atoms substituted by a hydrogen atom, $C_1$-$C_2$ alkyl radicals, phenyl radicals, and phenylalkyl groups, the alkyl group of which is a $C_1$-$C_4$ alkyl group.

6. The composition according to claim 1, wherein G is a G4 group; $R_1$, $R_4$, $R_5$, $R_8$ and $R_{11}$ denote hydrogen atoms; $R_2$ and $R_7$ are chosen from, independently of one another, hydrogen atoms, halogen atoms, alkoxy groups, and substituted and unsubstituted amino groups; $R_3$ and $R_6$ are chosen from, independently of one another, hydrogen atoms, halogen atoms, and substituted and unsubstituted amino groups; $R_9$ is chosen from hydrogen atoms, substituted and unsubstituted alkyl groups, alkoxy groups, aryl groups, and substituted and unsubstituted amino groups; $R_{10}$ is chosen from hydrogen atoms and alkyl radicals; A is chosen from substituted and unsubstituted benzene rings and substituted and unsubstituted pyridine rings; X is chosen from oxygen and sulphur atoms, direct bonds and $SO_2$ groups; $W_2$ is chosen from carbon atoms and nitrogen atoms; $Y_2$ is chosen from carbon atoms and nitrogen atoms; $Z_2$ is chosen from OH groups, carbon atoms substituted by a hydrogen atom, $C_1$-$C_4$ alkyl radicals, phenyl radicals, amino groups carrying two $C_1$-$C_4$ alkyl groups, the two radicals optionally forming, with the nitrogen atom carrying them, a saturated 5-membered heterocycle, nitrogen atoms, NH groups, nitrogen atoms substituted by hydrogen atoms, $C_1$-$C_2$ alkyl radicals, phenyl radicals, and phenylalkyl groups wherein the alkyl group is a $C_1$-$C_4$ alkyl group.

7. The composition according to claim 1, wherein G is a G5 group, X is chosen from an oxygen atom or a direct bond; $R_1$, $R_4$, $R_5$, $R_8$ and $R_{10}$ denote hydrogen atoms; $R_2$ and $R_7$ are chosen from, independently of one another, alkyl radicals, alkoxy radicals, and substituted and unsubstituted amino radicals; $R_3$ and $R_6$ are chosen from, independently of one another, hydrogen atoms, alkyl radicals, and substituted and unsubstituted amino radicals; $R_9$ is chosen from hydrogen atoms and substituted and unsubstituted amino radicals; and $R_{12}$ is chosen from substituted and unsubstituted alkyl radicals, substituted and unsubstituted aryl radicals, thienyl radicals, and furanyl radicals.

8. The composition according to claim 1, wherein G is a G6 group; X is chosen from a direct bond or an oxygen atom; $R_1$, $R_3$, $R_4$, $R_5$, $R_6$, $R_8$ and $R_{10}$ denote hydrogen atoms, $R_2$, $R_9$ and $R_7$ denote, independently of one another, substituted and unsubstituted amino groups; and $R_{12}$ is an alkyl radical.

9. A composition for the coloring of human keratinous fibers comprising, in a medium appropriate for dyeing comprising water and/or at least one organic solvent and, at least one compound chosen from the compounds of the following formulae:

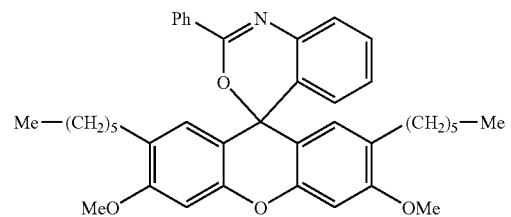

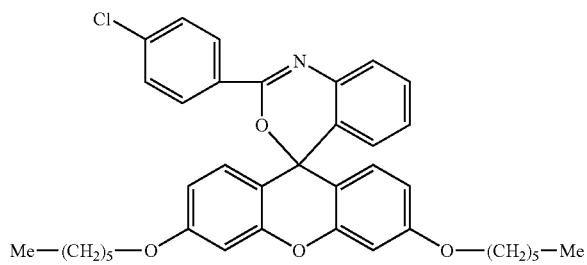

-continued
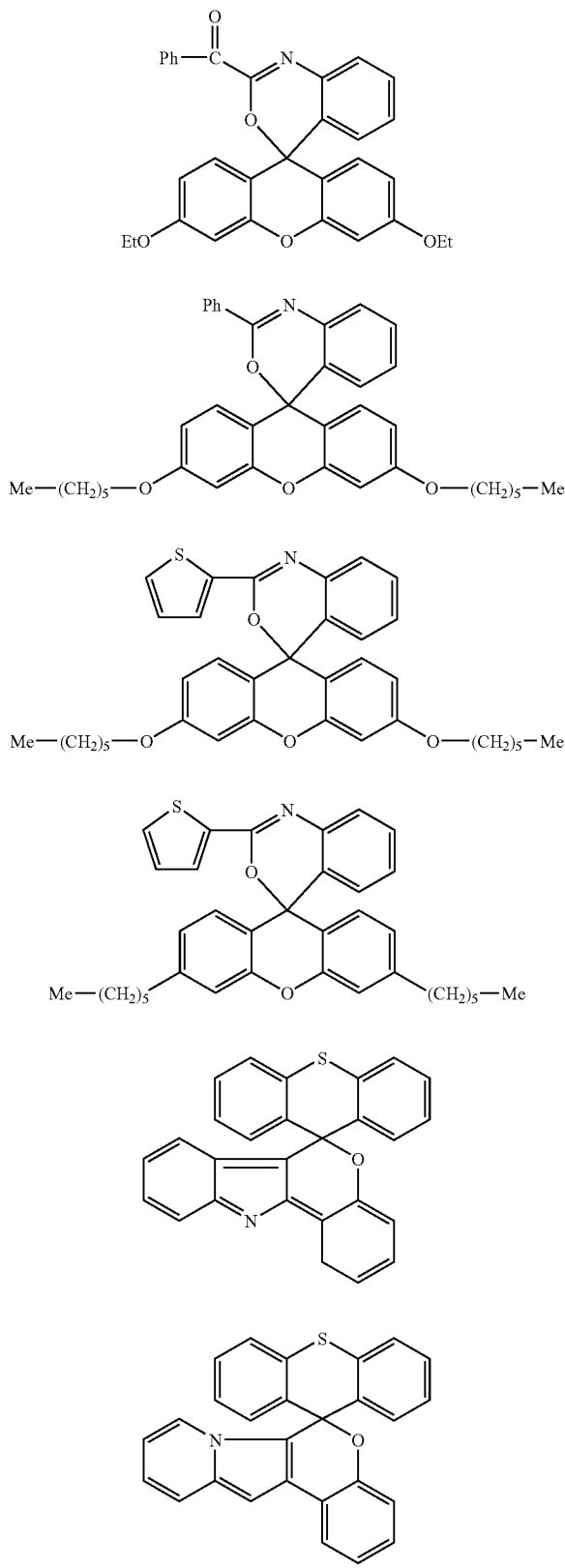

-continued
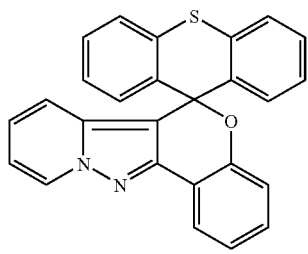
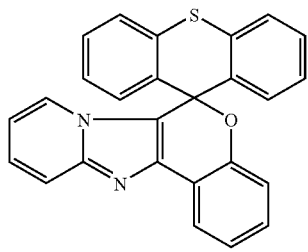
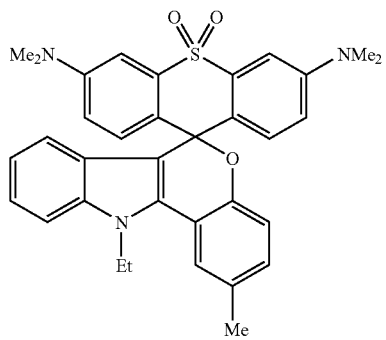
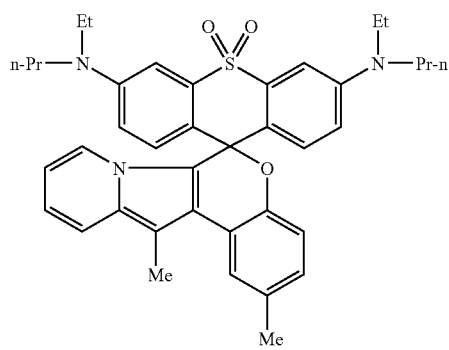
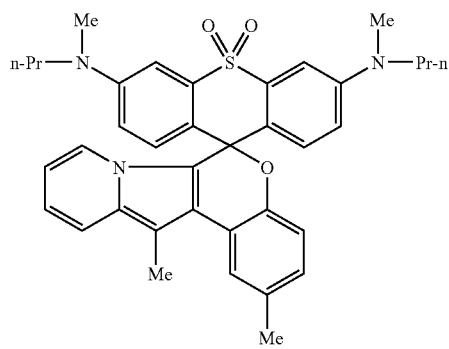

-continued
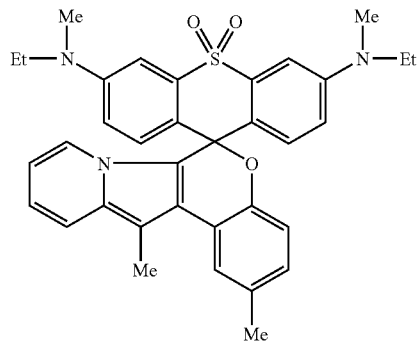
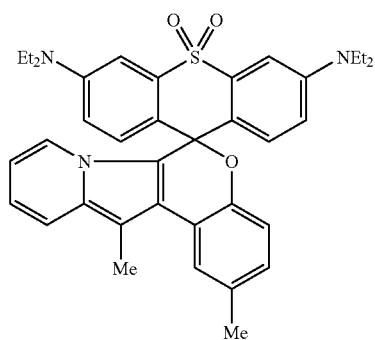
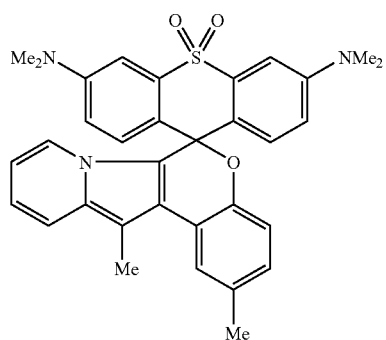
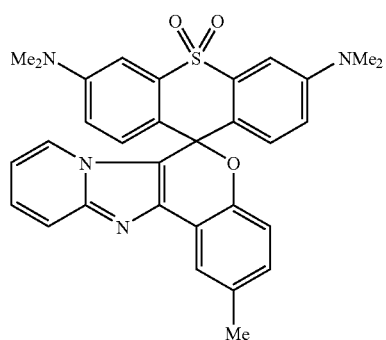

-continued
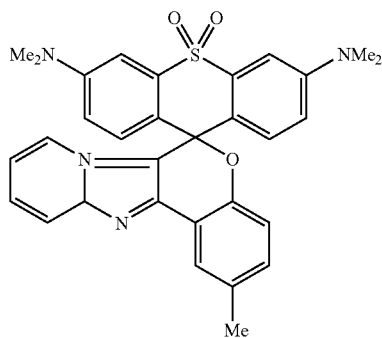
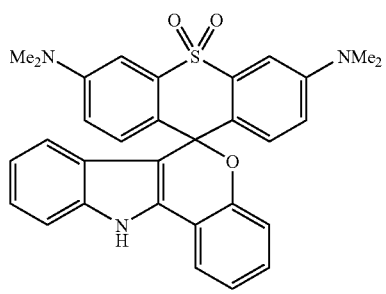
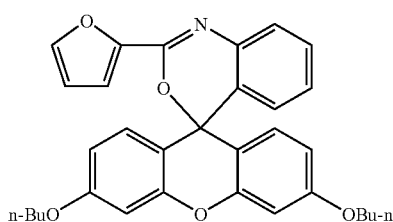
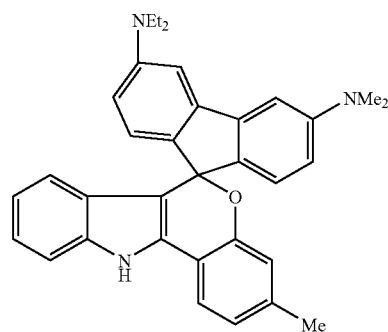
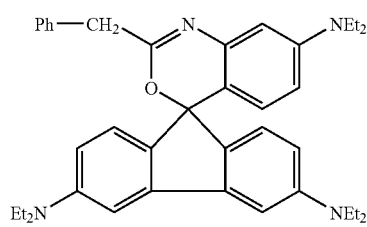

-continued
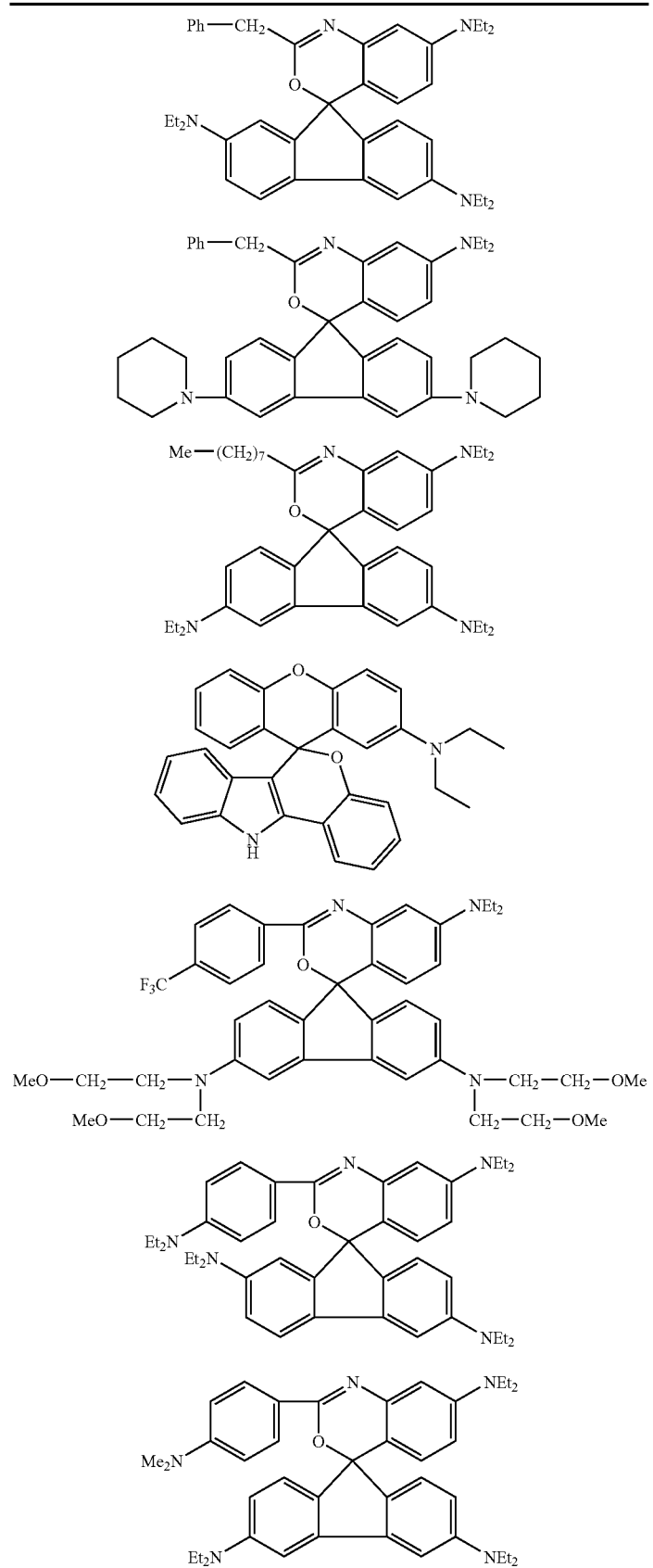

-continued
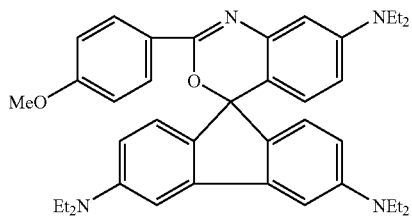
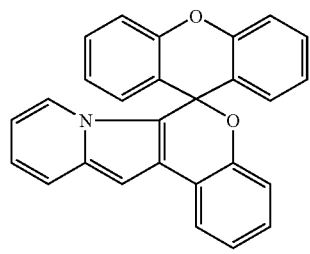
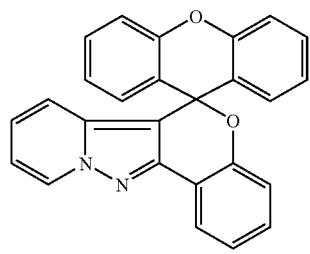
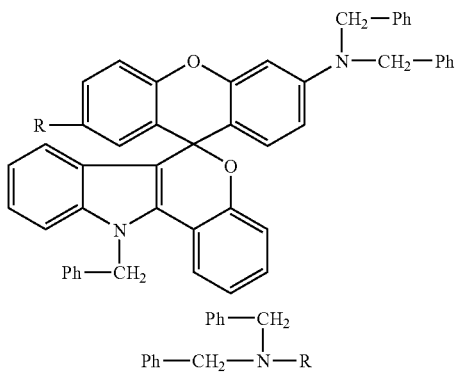
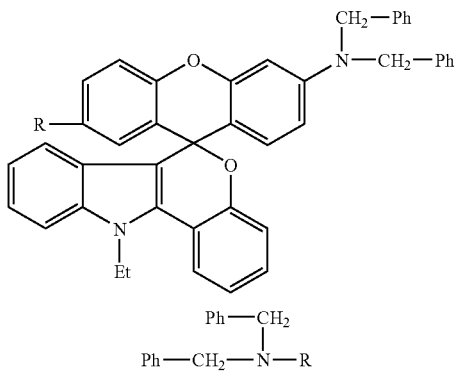

-continued
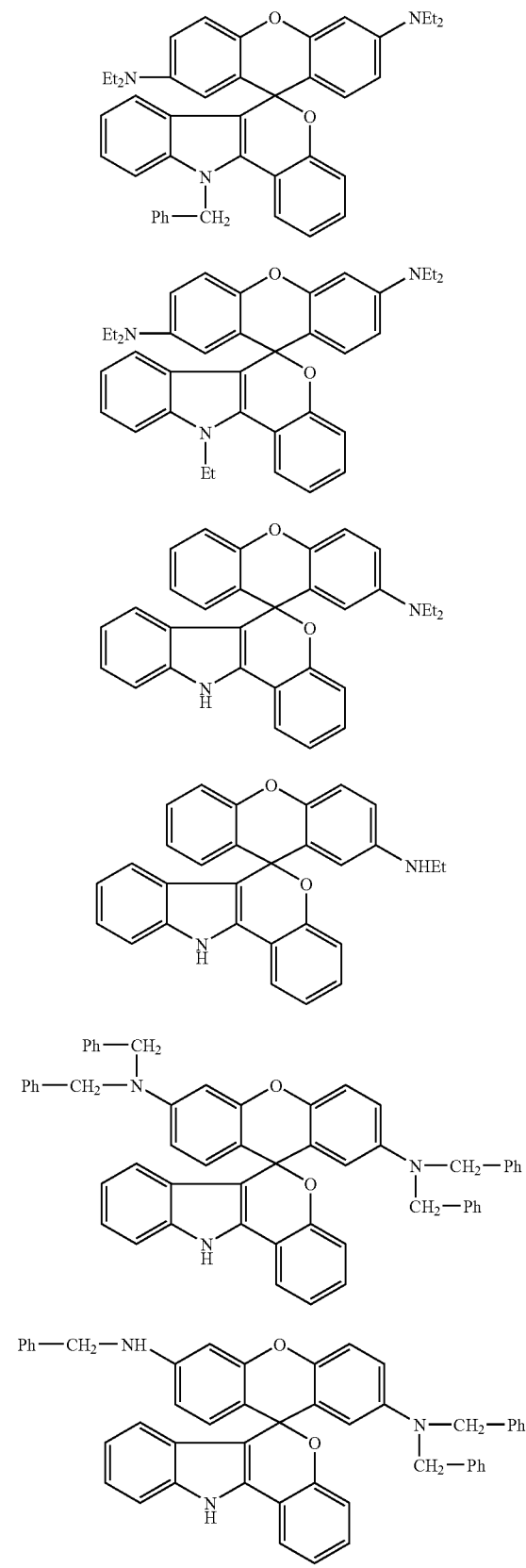

-continued
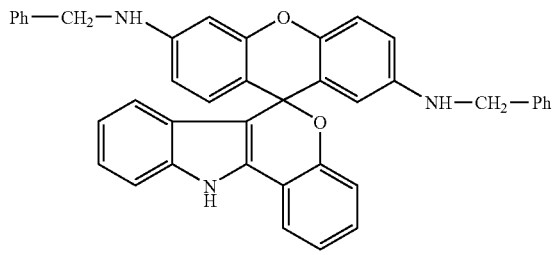
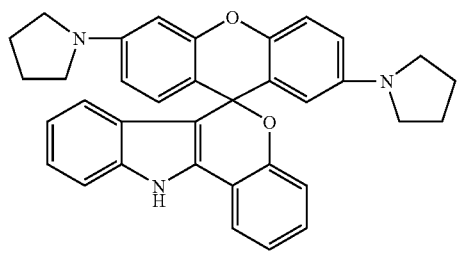
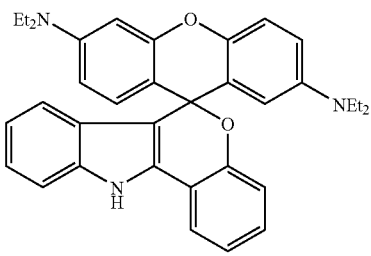
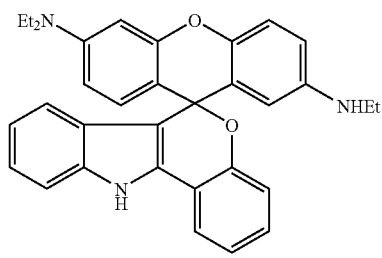
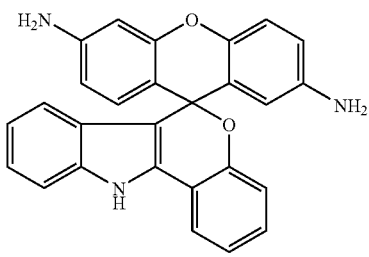
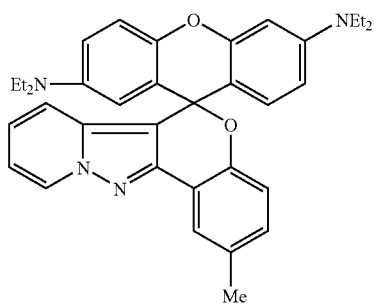

-continued
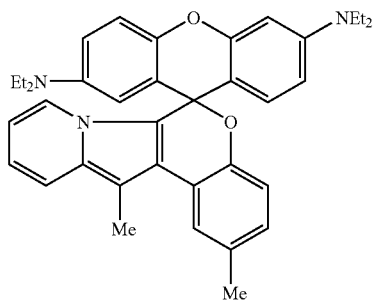
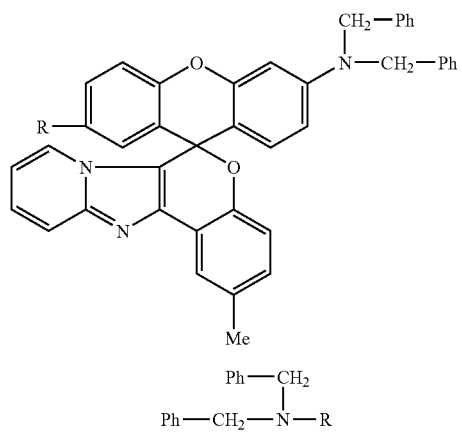
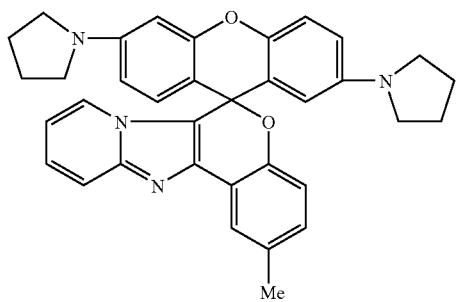
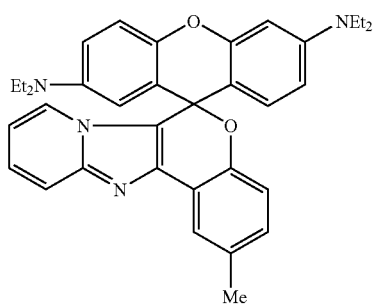

-continued
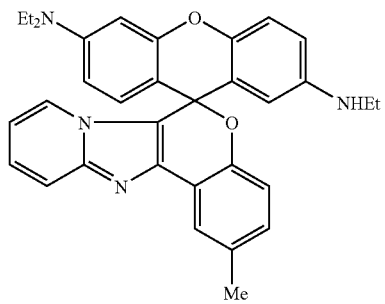
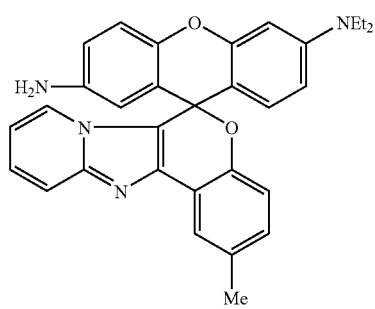
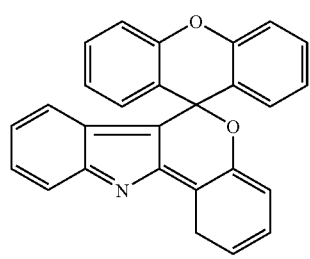
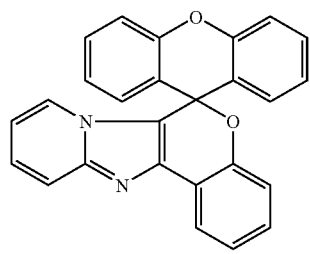
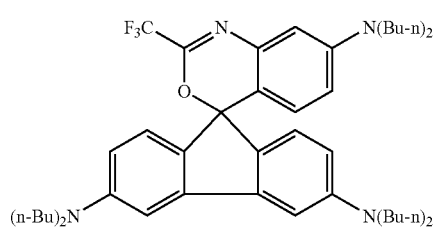
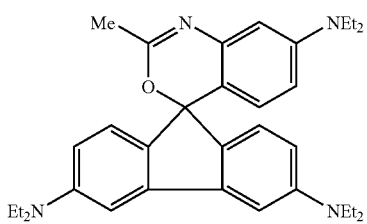

-continued
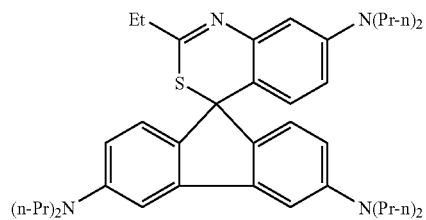
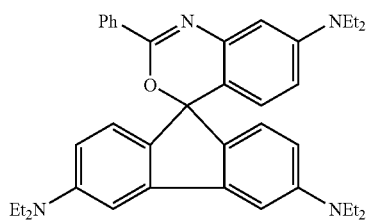
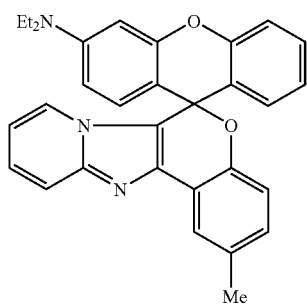
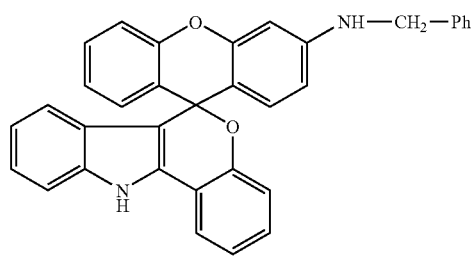
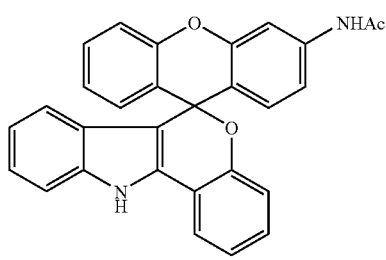
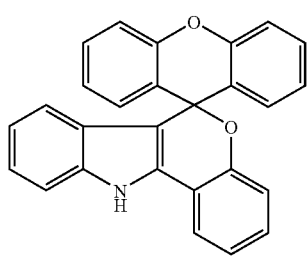

-continued
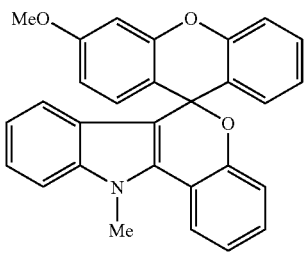
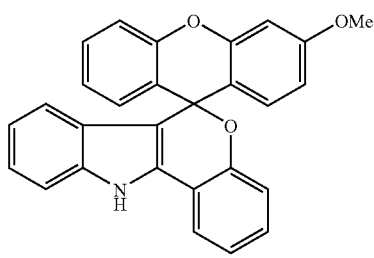
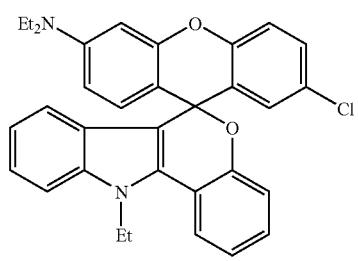
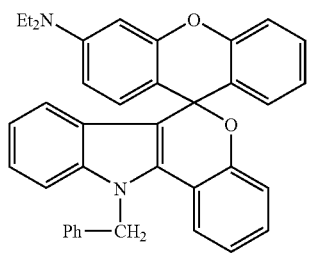
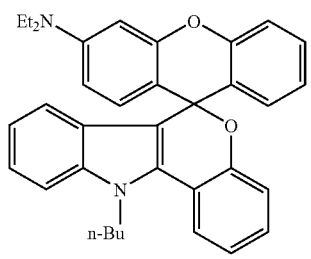
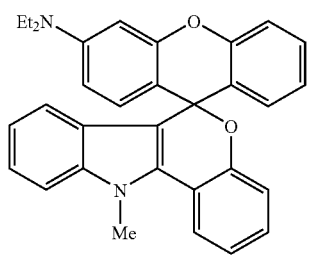

-continued
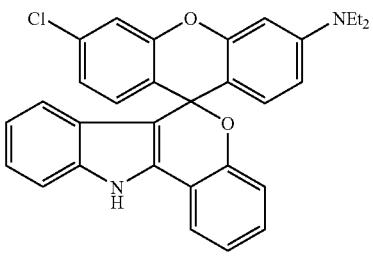
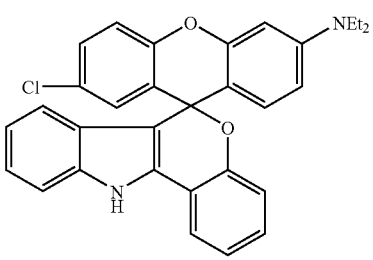
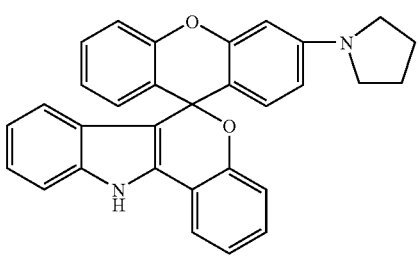
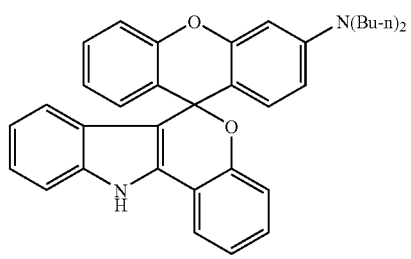
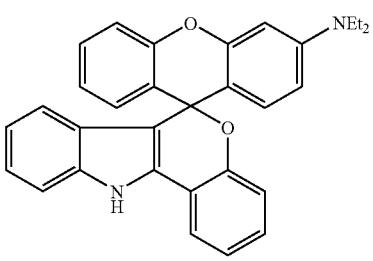
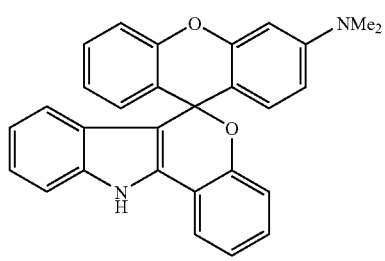

-continued
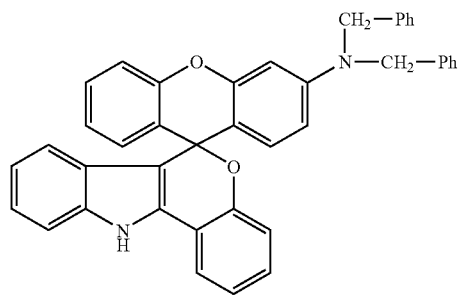
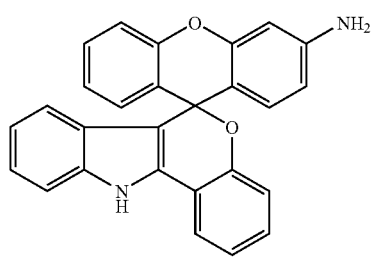
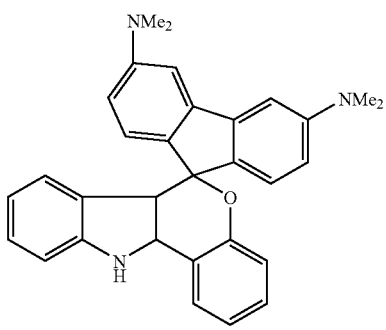
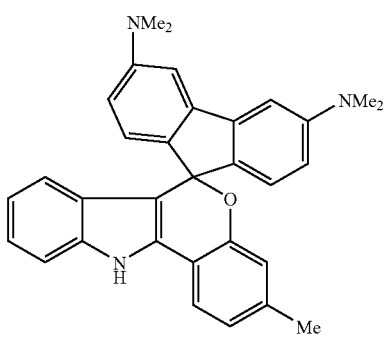
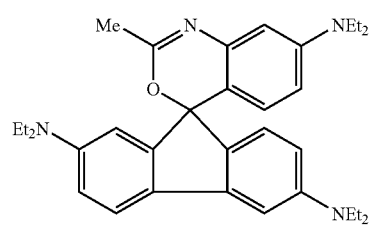

-continued
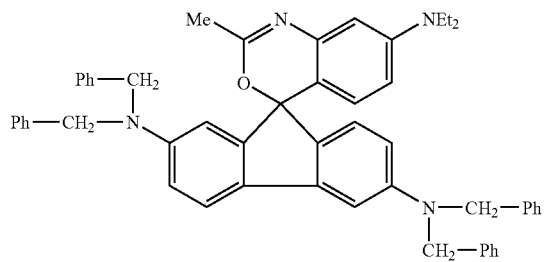
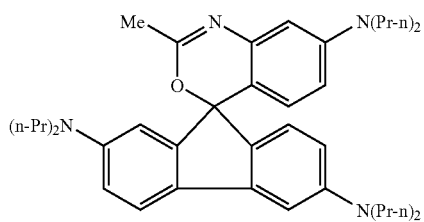
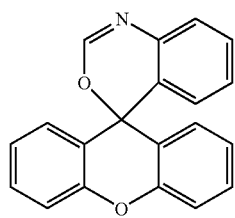
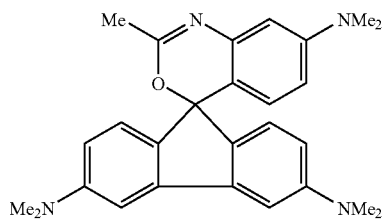
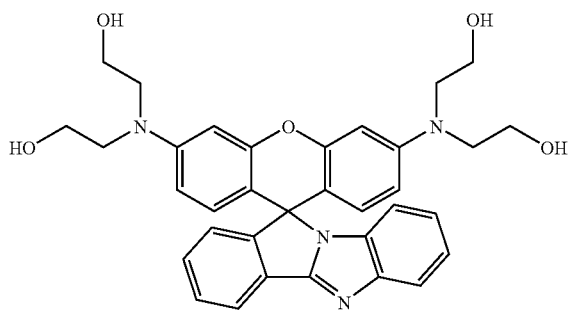
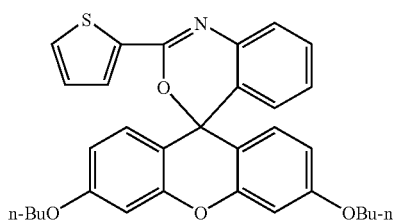

-continued
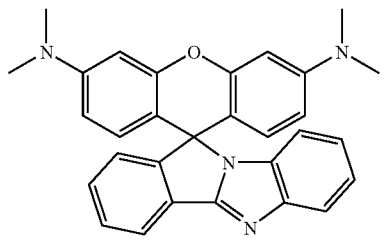
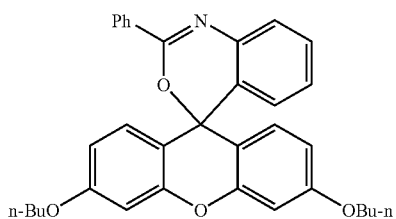
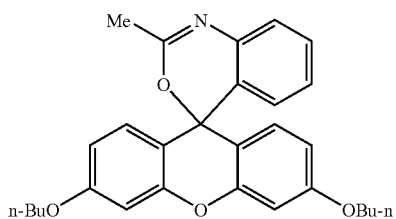
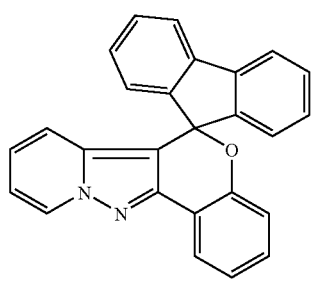
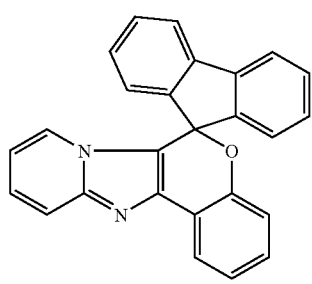

-continued
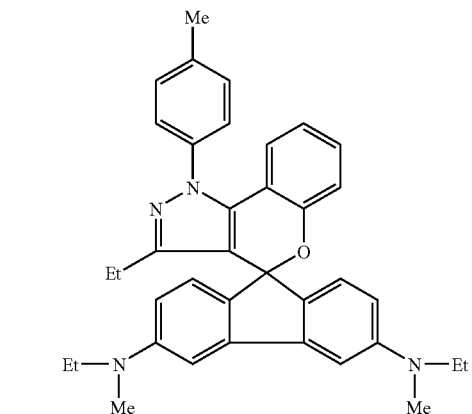
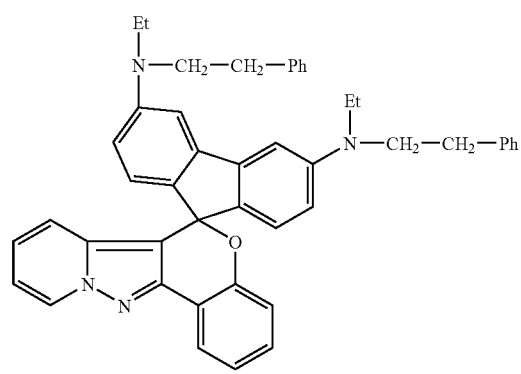
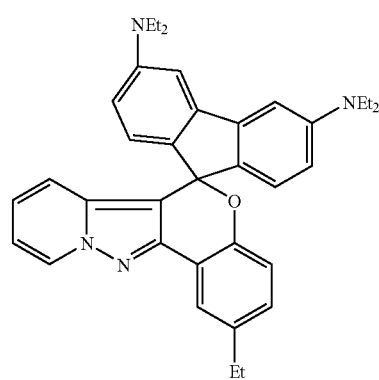
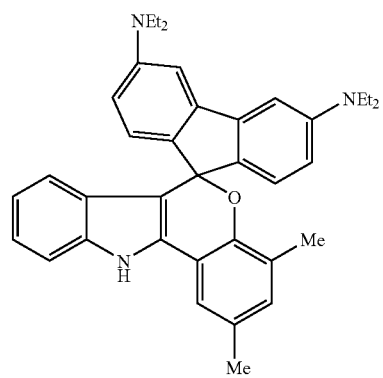

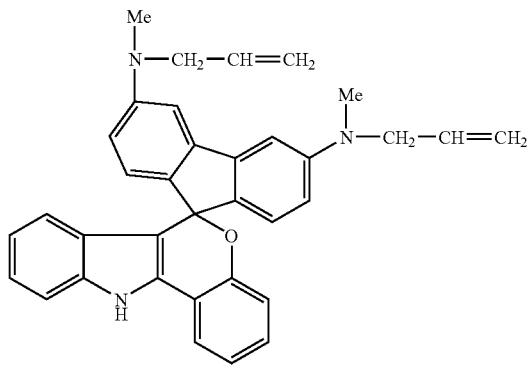
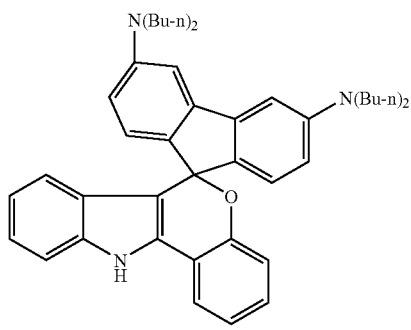
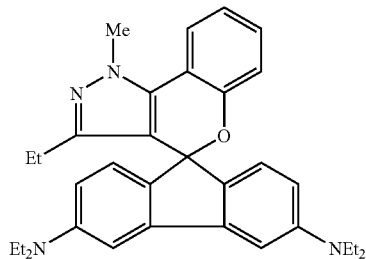
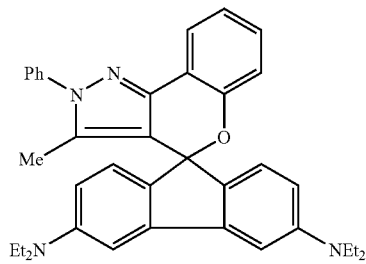
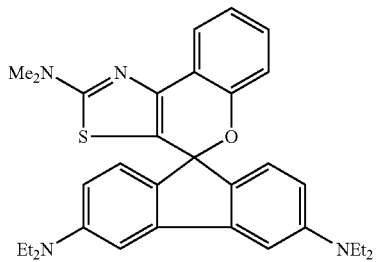

-continued
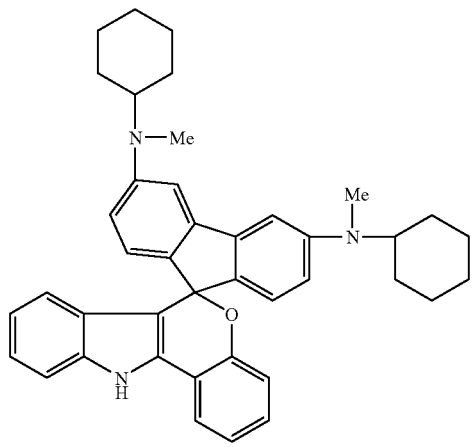
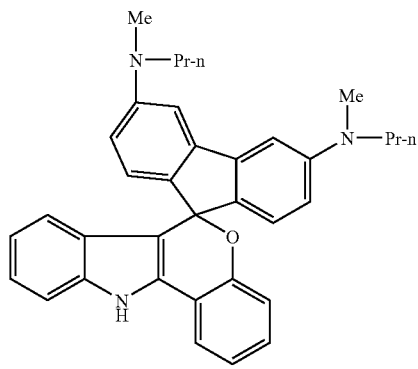
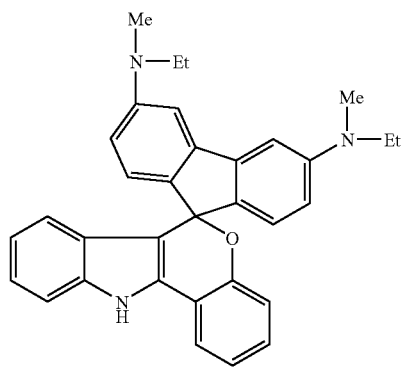
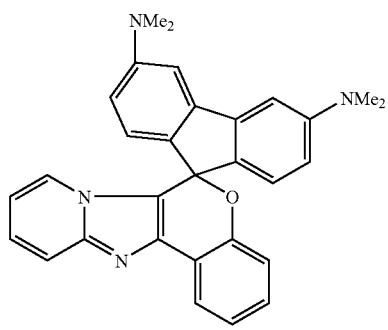

-continued
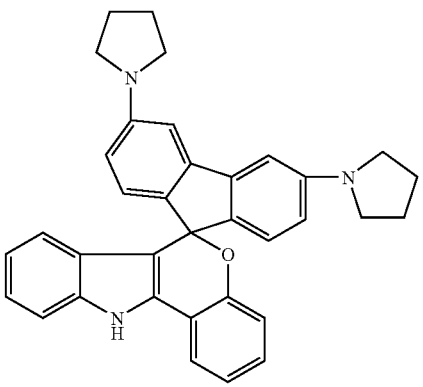
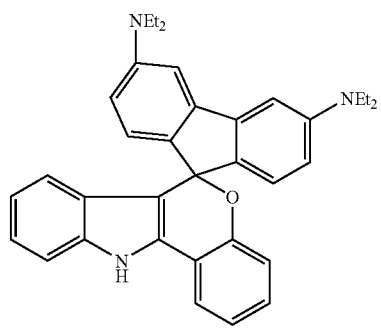
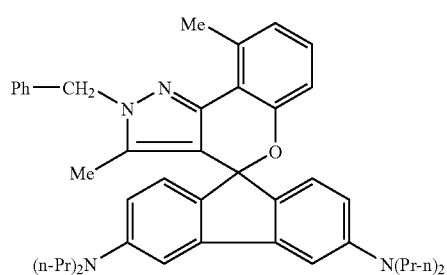
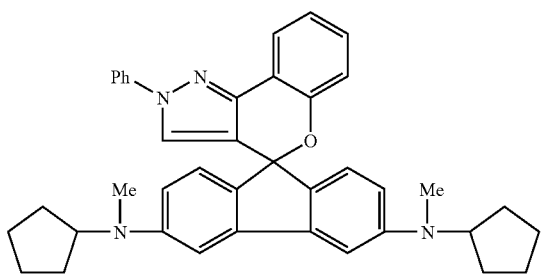
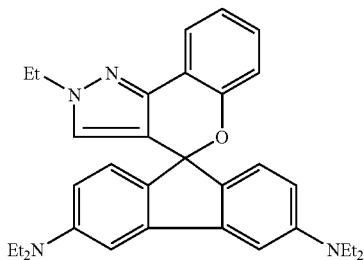

-continued
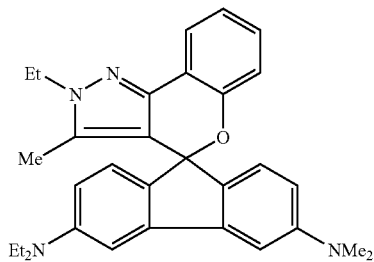
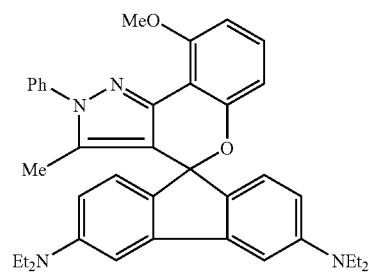
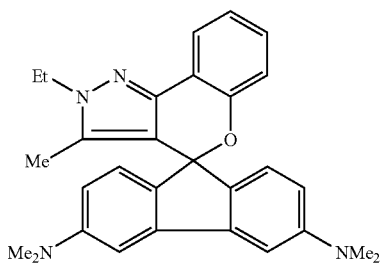
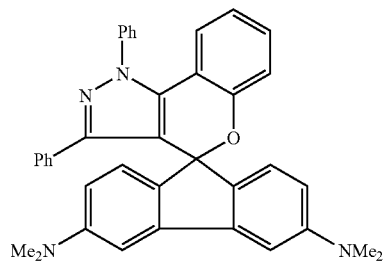
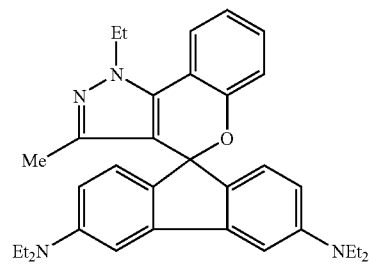

-continued
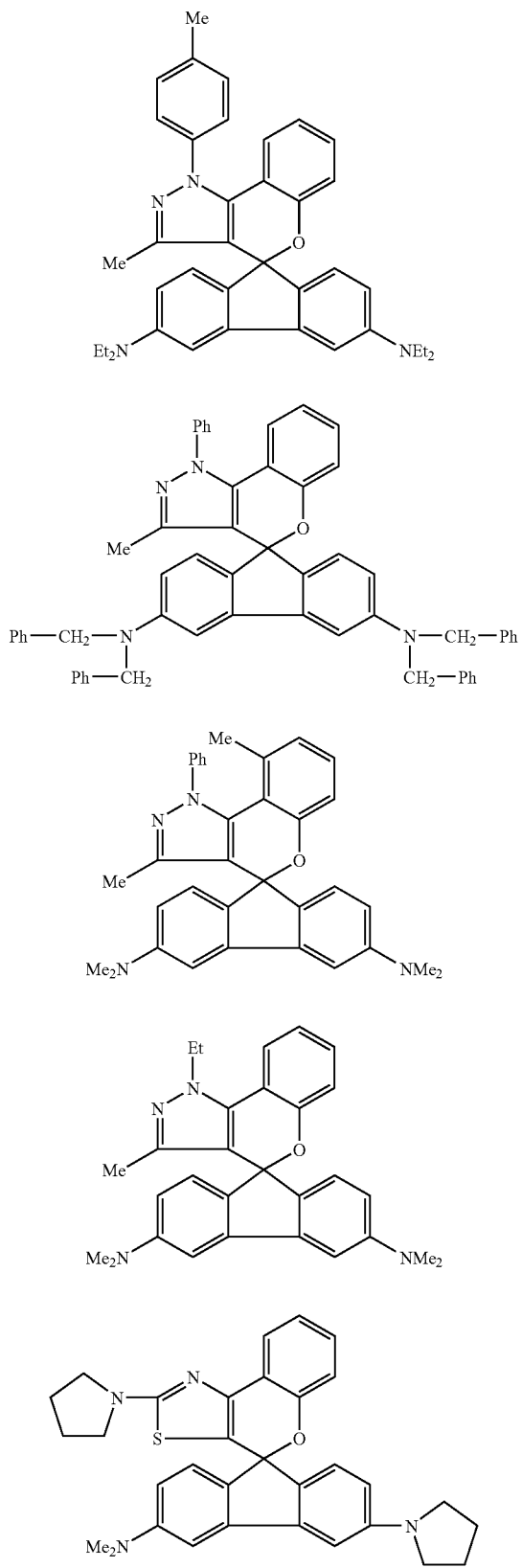

-continued
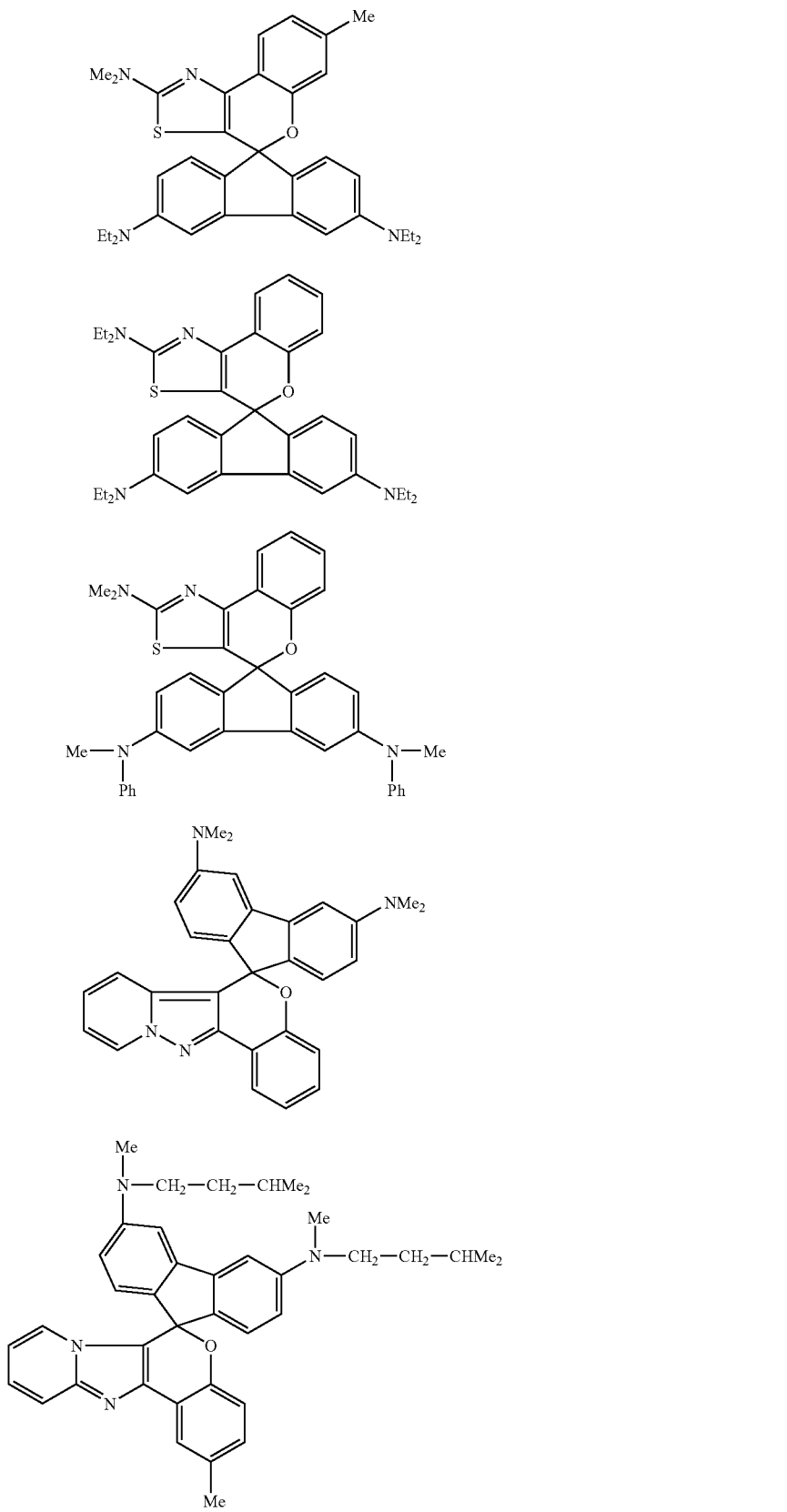

-continued
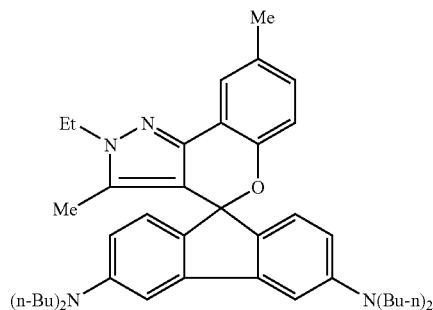
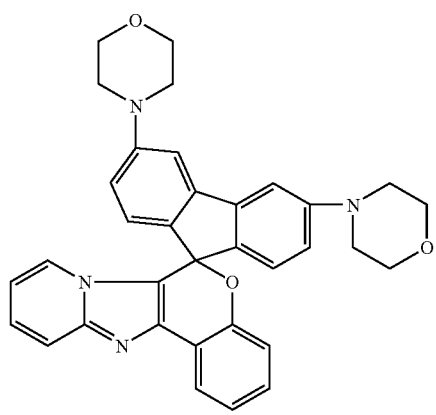
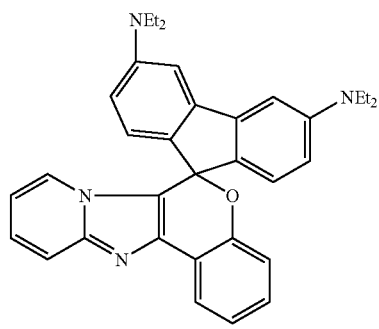
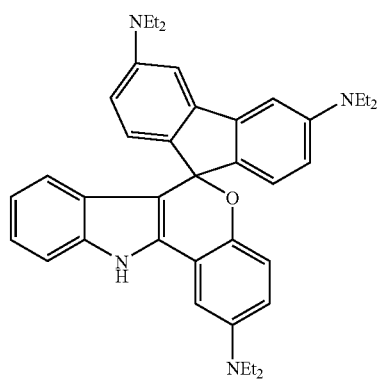

-continued
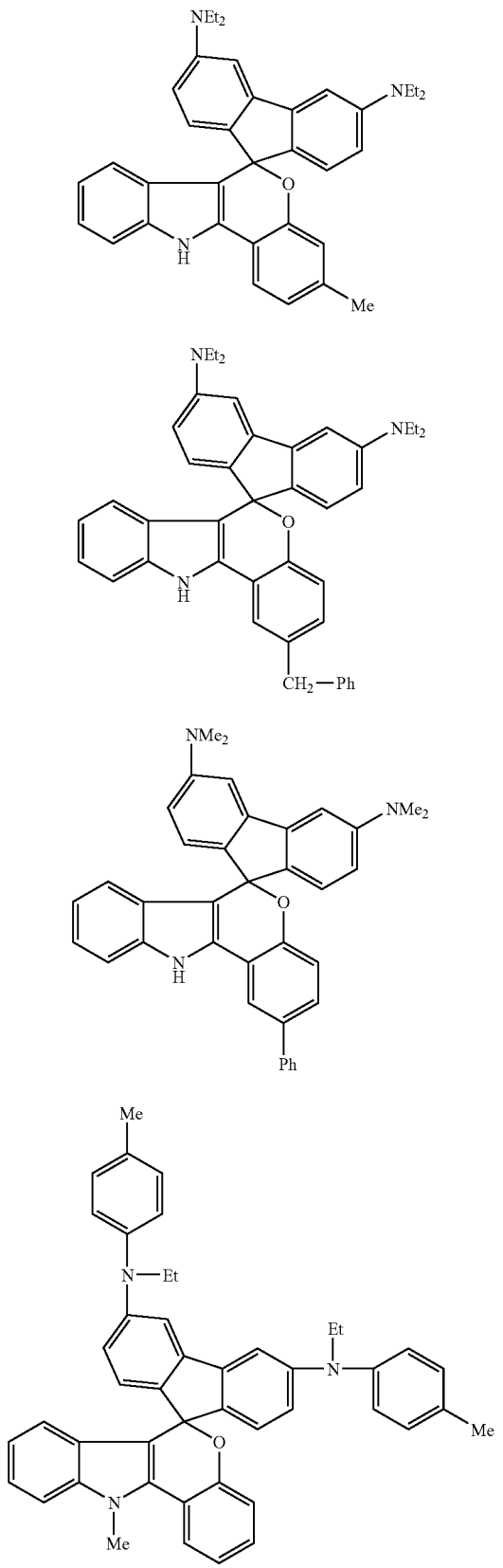

-continued
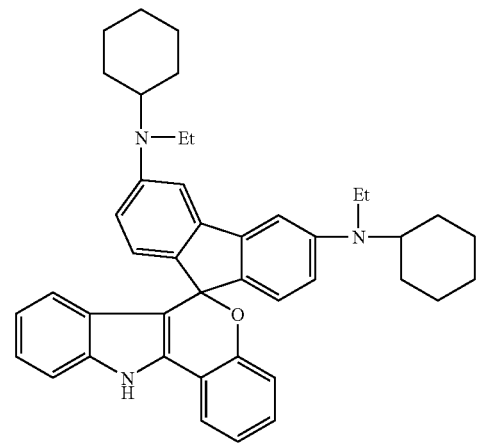
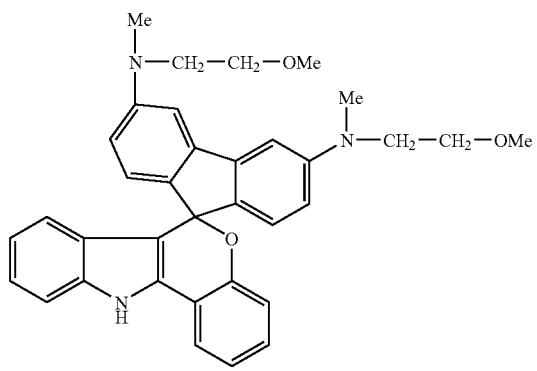
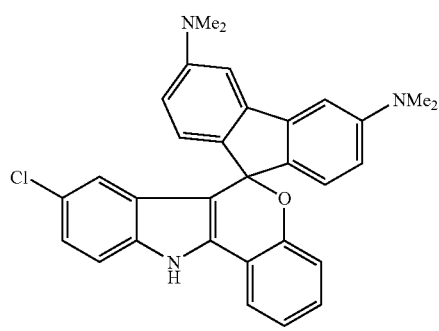
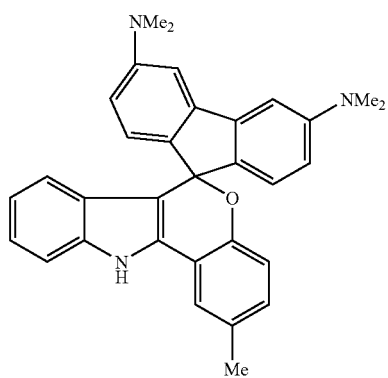

-continued
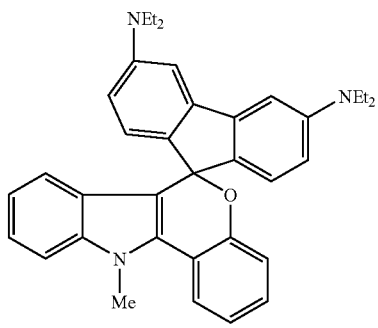
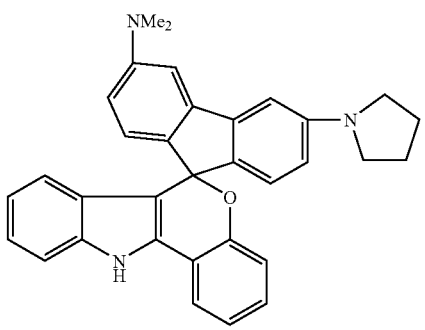
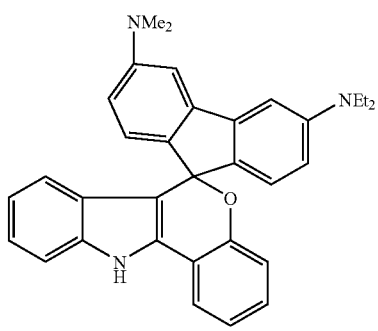
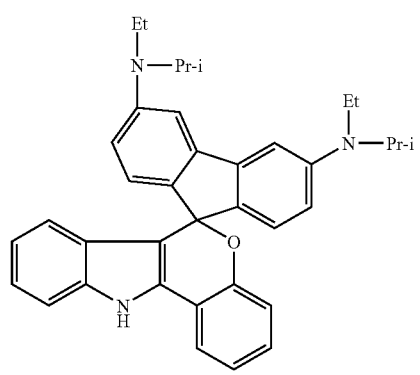

-continued
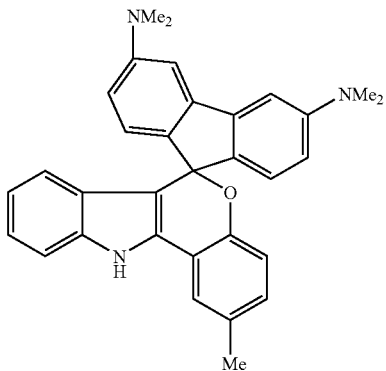
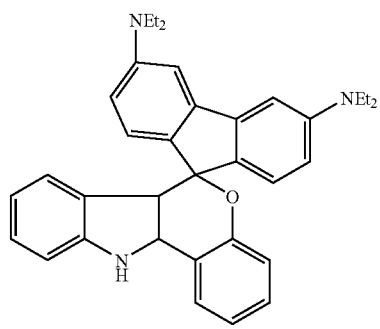
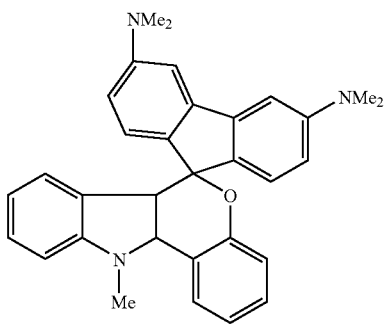
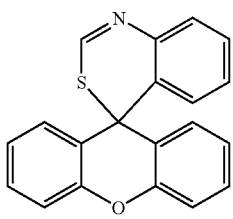
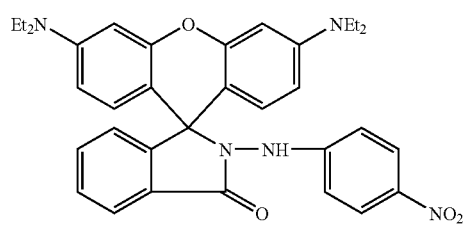

-continued
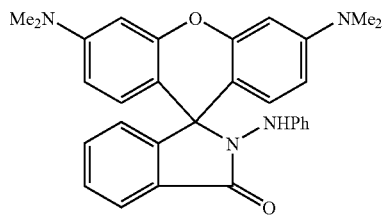
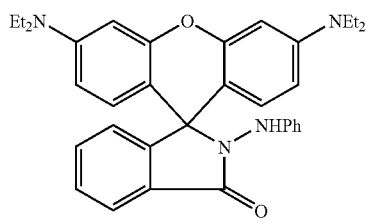
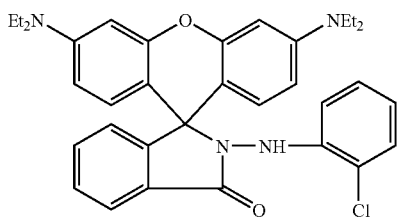
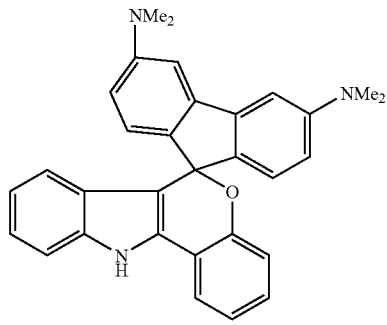
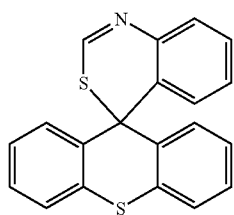
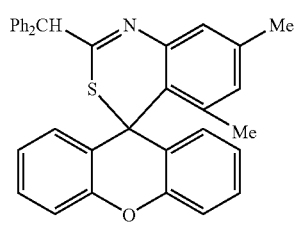

-continued
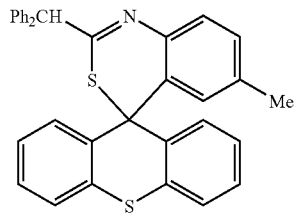
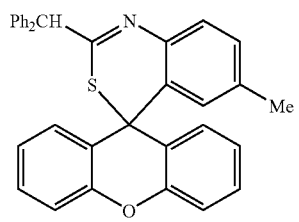
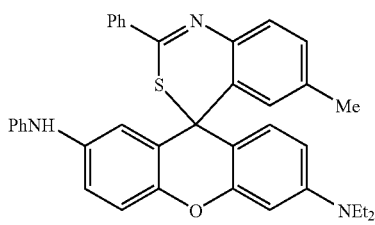
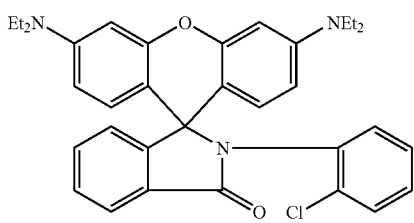
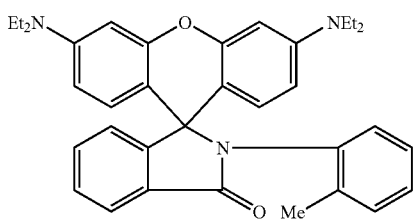
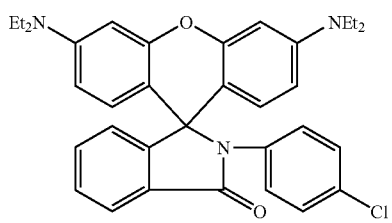
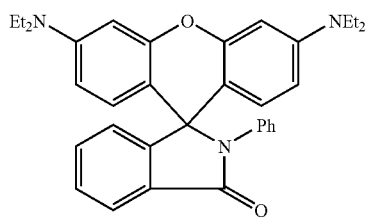

-continued

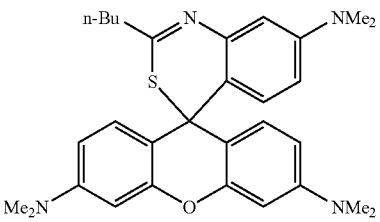

and wherein the pH of the composition ranges from 3 to 12; and the composition is appropriate for coloring human keratinous fibers.

10. The composition according to claim 9, wherein at least one compound is chosen from the compounds of the following formulae:

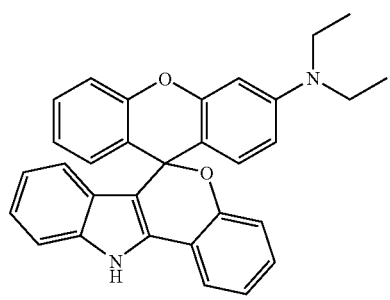

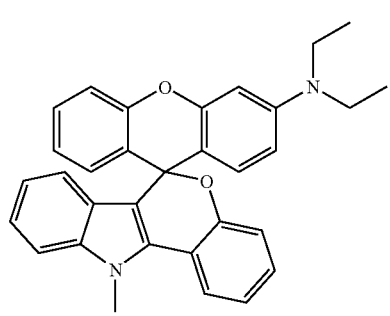

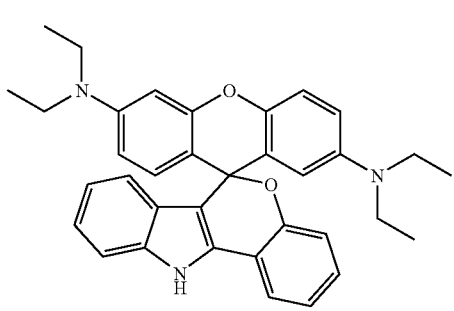

-continued

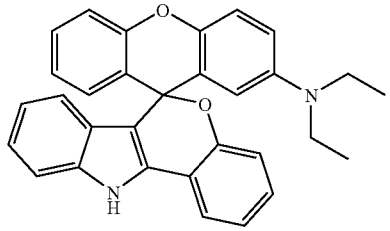

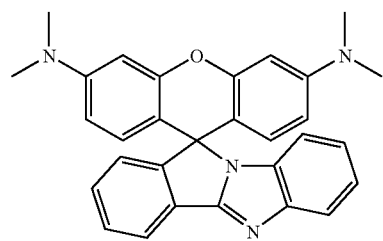

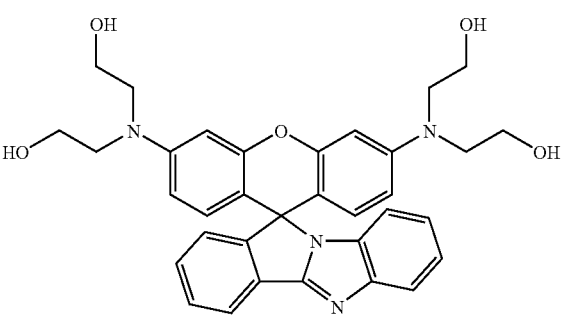

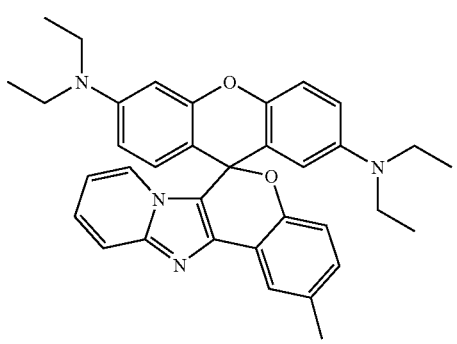

11. The composition according to claim 1, wherein the at least one compound is present in an amount ranging from 0.001 to 10% by weight, relative to the total weight of the composition.

12. A method for the treatment of keratinous fibers, comprising:
applying to the keratinous fibers, for a sufficient development time, a dyeing composition comprising, in a medium appropriate for dyeing, at least one compound chosen from the compounds of formula (I) comprising a cyclic group G including a ring H capable of opening, the dyes corresponding to the compounds of formula (I) wherein the ring H is open, and the addition salts thereof:

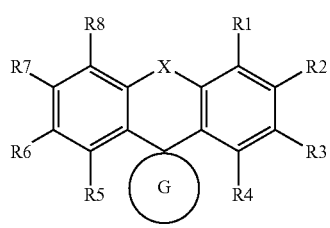

wherein:
$R_1$, $R_2$, $R_3$, $R_4$, $R_5$, $R_6$, $R_7$ and $R_8$ are chosen from, independently of one another:
hydrogen atoms;
halo radicals;
hydroxyl radicals;
nitro radicals;
amino radicals;
carboxyl radicals;
aminocarbonyl radicals;
cyano radicals; and
radicals resulting from a hydrocarbon chain comprising from 1 to 100 carbon atoms, wherein the hydrocarbon chain is linear or branched, acyclic or mono- or polycyclic, fused or unfused, saturated or unsaturated, aromatic or nonaromatic, and optionally interrupted by at least one heteroatom chosen from nitrogen, oxygen and sulphur atoms or by at least one carbonyl group, which can be terminated by a hydrocarbonyl group or by a group comprising at least one heteroatom chosen from nitrogen, oxygen and sulphur atoms, which begins with a carbonyl group or with a group comprising at least one heteroatom chosen from nitrogen, oxygen and sulphur atoms, and which can be substituted by at least one group chosen from the following radicals: hydroxyl, halo, carboxyl, carboxy ($C_1$-$C_9$)alkyl, cyano, amino and $C_1$-$C_6$ alkoxy;
it being possible for at least two of the $R_1$, $R_2$, $R_3$, $R_4$, $R_5$, $R_6$, $R_7$ and $R_8$ radicals carried by two adjacent carbon atoms to form, together and with the carbon atoms to which they are attached, at least one fused or unfused, aromatic, mono- or polycarbocyclic group comprising from 5 to 20 ring members, it being possible for at least one carbon atom to be replaced by an oxygen, nitrogen, sulphur or phosphorus atom, the aromatic mono- or polycarbocyclic group being unsubstituted or substituted by at least one radical chosen from a halo, hydroxyl, amino, carboxyl or $C_6$-$C_{18}$ aryl and cyano radicals;
the amino radicals being unsubstituted or substituted by one or two identical or different radicals chosen from $C_1$-$C_9$ alkyl radicals; $C_1$-$C_9$ hydroxyalkyl radicals; $C_2$-$C_9$ alkenyl radicals; $C_6$-$C_{12}$ cycloalkyl radicals; $C_6$-$C_{18}$ aryl radicals optionally substituted by at least one radical chosen from halo or $C_1$-$C_9$ alkyl radicals; ($C_6$-$C_{18}$)arylcarbonyl radicals; cyclo ($C_6$-$C_{12}$)alkyl($C_1$-$C_9$)alkyl radicals; ($C_6$-$C_{18}$)aryl($C_1$-$C_9$) alkyl radicals; ($C_1$-$C_9$)alkylcarbonyl radicals; ($C_1$-$C_9$) alkoxycarbonyl($C_1$-$C_9$)alkyl radicals; α-naphthylalkyl radicals; $C_1$-$C_9$ haloalkyl radicals; $C_1$-$C_9$ cyanoalkyl radicals; $C_2$-$C_{15}$ acyl radicals; ($C_1$-$C_9$)alkoxycarbonyl radicals; ($C_6$-$C_{18}$)aryloxycarbonyl radicals; ($C_6$-$C_{18}$)aryloxy($C_1$-$C_9$)alkylcarbonyl radicals; ($C_6$-$C_{18}$)aryl($C_1$-$C_9$)alkoxycarbonyl radicals; ($C_1$-$C_9$)alkoxy($C_6$-$C_{18}$)arylcarbonyl radicals; ($C_1$-$C_9$) alkoxy($C_1$-$C_9$)alkylcarbonyl radicals; di($C_1$-$C_9$) alkylaminocarbonyl radicals; di($C_1$-$C_9$)alkylaminosulphonyl radicals; ($C_1$-$C_9$)alkyl($C_6$-$C_{18}$)arylsulphonyl radicals; ($C_1$-$C_9$)alkylsulphonyl radicals; di($C_1$-$C_9$)alkylamino($C_1$-$C_9$) alkyl radicals; and ($C_1$-$C_9$)alkoxy($C_1$-$C_9$)alkyl radicals;

it being possible, when the amino radicals are substituted by two radicals, for the latter to form, with the nitrogen atom of the amino radical, a 5- or 6-membered heterocycle optionally comprising at least one additional heteroatom;

X represents a direct bond or a divalent atom, or a sulphone $SO_2$ or $C(R_{13})_2$ or $NR_{13}$ group;

G represents a divalent radical chosen from the formulae G1 to G7:

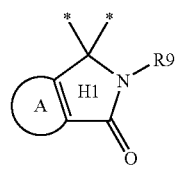

G1

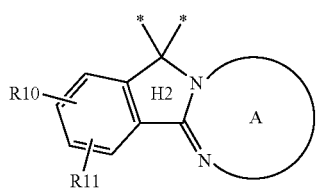

G2

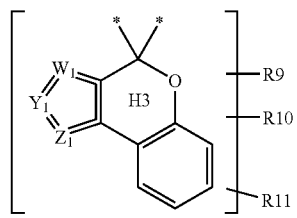

G3

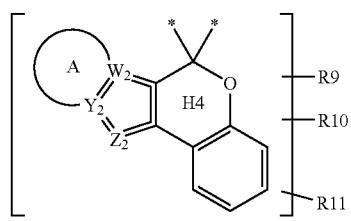

G4

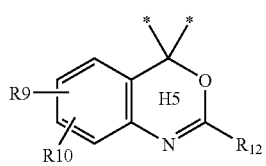

G5

-continued

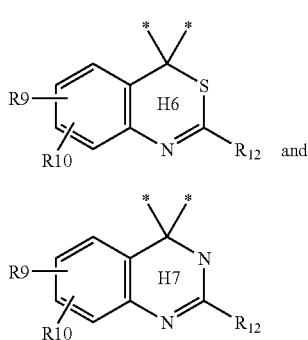

wherein:
Y$_1$, W$_1$ and Z$_1$, on the one hand, and Y$_2$, W$_2$ and Z$_2$, on the other hand, are chosen from, independently of one another, carbon atoms, nitrogen atoms, sulphur atoms and divalent groups CR$_{13}$ and NR$_{13}$;
R$_9$, R$_{10}$, R$_{11}$ and R$_{13}$ have the same definitions as R$_1$;
R$_{12}$ is chosen from:
  hydrogen atoms;
  C$_1$-C$_9$ alkyl radicals;
  amino radicals;
  C$_1$-C$_9$ alkoxy radicals;
  C$_6$-C$_{18}$ aryl radicals, which are unsubstituted or substituted by at least one group chosen from hydrogen atoms, hydroxyl radicals, C$_1$-C$_9$ alkyl radicals, C$_6$-C$_{18}$ aryl radicals, C$_6$-C$_{18}$ aryloxy radicals, C$_1$-C$_9$ alkoxy radicals, halo radicals, carboxyl radicals, cyano radicals and amino radicals which are substituted or unsubstituted;
  furanyl radicals;
  (C$_1$-C$_9$)alkylthio radicals;
  thienyl radicals;
  phenylcarbonyl radicals;
  trifluoroalkyl radicals; and
  di(C$_6$-C$_{18}$)aryl(C$_1$-C$_9$)alkyl radicals; and
A represents a C$_6$-C$_{18}$ aryl group or a heterocyclic group which is saturated or unsaturated and substituted or unsubstituted, comprising from 5 to 12 ring members, wherein the pH is adjusted using at least one first acidifying agent or at least one first basifying agent according to the coloring desired; and
  optionally modifying of the coloring of the keratinous fibers by applying at least one second acidifying agent or at least one second basifying agent to the keratinous fibers.

13. The method according to claim 12, wherein, the at least one first acidifying agent or the at least one first basifying agent is mixed with the dyeing composition before applying to the keratinous fibers.

14. The method according to claim 12, wherein, the at least one first acidifying agent or the at least one first basifying agent is applied to the keratinous fibers either before or after the dyeing composition.

15. The method according to claim 12, wherein the at least one acidifying agent is chosen from inorganic acids and organic acids.

16. The method according to claim 12, wherein the at least one basifying agent is chosen from:
  basic amino acids;
  alkali metal and alkaline earth metal carbonates and bicarbonates;
  silicates and metasilicates;

compounds of formula (II):

$$X(OH)_n \quad (II)$$

wherein:
  X is chosen from potassium, lithium, sodium, and ammonium N$^+$R$_{15}$R$_{16}$R$_{17}$R$_{18}$ ions with R$_{15}$, R$_{16}$, R$_{17}$ and R$_{18}$, which are identical or different, denoting C$_2$-C$_4$ alkyl radicals, when n is equal to 1;
  X is chosen from magnesium and calcium atoms, when n is equal to 2;
compounds of formula (III):

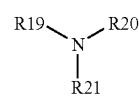

wherein:
  R$_{19}$ is chosen from hydrogen atoms, C$_1$-C$_6$ alkyl radicals, C$_1$-C$_6$ monohydroxyalkyl radicals and C$_2$-C$_6$ polyhydroxyalkyl radicals;
  R$_{20}$ and R$_{21}$, which are identical or different, are chosen from hydrogen atoms, C$_1$-C$_6$ alkyl radicals, C$_1$-C$_6$ monohydroxyalkyl radicals and C$_2$-C$_6$ polyhydroxyalkyl radicals;
compounds of formula (IV):

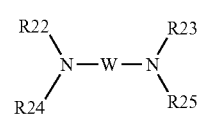

wherein:
  W is a propylene residue optionally substituted by a hydroxyl group or a C$_1$-C$_4$ alkyl radical;
  R$_{22}$, R$_{23}$, R$_{24}$ and R$_{25}$, which are identical or different, are chosen from hydrogen atoms, C$_1$-C$_4$ alkyl radicals and C$_1$-C$_4$ hydroxyalkyl radicals.

17. A multi-compartment kit comprising, in at least one first compartment, at least one composition comprising, in a medium appropriate for dyeing, at least one compound chosen from the compounds of formula (I) comprising a cyclic group G including a ring H capable of opening, the dyes corresponding to the compounds of formula (I) wherein the ring H is open, and the addition salts thereof:

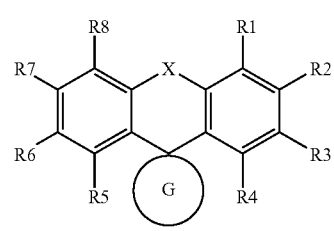

wherein:
  R$_1$, R$_2$, R$_3$, R$_4$, R$_5$, R$_8$, R$_7$ and R$_8$ are chosen from, independently of one another:
    hydrogen atoms;
    halo radicals;
    hydroxyl radicals;

nitro radicals;
amino radicals;
carboxyl radicals;
aminocarbonyl radicals;
cyano radicals; and
radicals resulting from a hydrocarbon chain comprising from 1 to 100 carbon atoms, wherein the hydrocarbon chain is linear or branched, acyclic or mono- or polycyclic, fused or unfused saturated or unsaturated, aromatic or nonaromatic, and optionally interrupted by at least one heteroatom chosen from nitrogen, oxygen and sulphur atoms or by at least one carbonyl group, which can be terminated by a hydrocarbonyl group or by a group comprising at least one heteroatom chosen from nitrogen, oxygen and sulphur atoms, which begins with a carbonyl group or with a group comprising at least one heteroatom chosen from nitrogen, oxygen and sulphur atoms, and which can be substituted by at least one group chosen from the following radicals: hydroxyl, halo, carboxyl, carboxy($C_1$-$C_9$)alkyl, cyano, amino and $C_1$-$C_6$ alkoxy;

it being possible for at least two of the $R_1$, $R_2$, $R_3$, $R_4$, $R_5$, $R_6$, $R_7$ and $R_8$ radicals carried by two adjacent carbon atoms to form, together and with the carbon atoms to which they are attached, at least one fused or unfused, aromatic, mono- or polycarbocyclic group comprising from 5 to 20 ring members, it being possible for at least one carbon atom to be replaced by an oxygen, nitrogen, sulphur or phosphorus atom, the aromatic mono- or polycarbocyclic group being unsubstituted or substituted by at least one radical chosen from a halo, hydroxyl, amino, carboxyl or $C_6$-$C_{18}$ aryl and cyano radicals the amino radicals being unsubstituted or substituted by one or two identical or different radicals chosen from $C_1$-$C_9$ alkyl radicals; $C_1$-$C_9$ hydroxyalkyl radicals; $C_2$-$C_9$ alkenyl radicals; $C_6$-$C_{12}$ cycloalkyl radicals; $C_6$-$C_{18}$ aryl radicals optionally substituted by at least one radical chosen from halo or $C_1$-$C_9$ alkyl radicals; ($C_6$-$C_{18}$)arylcarbonyl radicals; cyclo($C_6$-$C_{12}$)alkyl($C_1$-$C_9$)alkyl radicals; ($C_6$-$C_{18}$)aryl($C_1$-$C_9$)alkyl radicals; ($C_1$-$C_9$)alkylcarbonyl radicals; ($C_1$-$C_9$)alkoxycarbonyl ($C_1$-$C_9$)alkyl radicals; α-naphthylalkyl radicals; $C_1$-$C_9$ haloalkyl radicals; $C_1$-$C_9$ cyanoalkyl radicals; $C_2$-$C_{15}$ acyl radicals; ($C_1$-$C_9$)alkoxycarbonyl radicals; ($C_6$-$C_{18}$) aryloxycarbonyl radicals; ($C_6$-$C_{18}$)aryloxy($C_1$-$C_9$)alkylcarbonyl radicals; ($C_6$-$C_{18}$)aryl($C_1$-$C_9$)alkoxycarbonyl radicals; ($C_1$-$C_9$)alkoxy($C_6$-$C_{18}$)arylcarbonyl radicals; ($C_1$-$C_9$)alkoxy($C_1$-$C_9$)alkylcarbonyl radicals; di($C_1$-$C_9$) alkylaminocarbonyl radicals; di($C_1$-$C_9$)alkylaminosulphonyl radicals; ($C_1$-$C_9$)alkyl($C_6$-$C_{18}$)arylsulphonyl radicals; ($C_1$-$C_9$)alkylsulphonyl radicals; di($C_1$-$C_9$) alkylamino($C_1$-$C_9$)alkyl radicals; and ($C_1$-$C_9$)alkoxy ($C_1$-$C_9$)alkyl radicals;

it being possible, when the amino radicals are substituted by two radicals, for the latter to form, with the nitrogen atom of the amino radical, a 5- or 6-membered heterocycle optionally comprising at least one additional heteroatom;

X represents a direct bond or a divalent atom, or a sulphone $SO_2$ or $C(R_{13})_2$ or $NR_{13}$ group;

G represents a divalent radical chosen from the formulae G1 to G7:

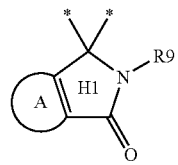

G1

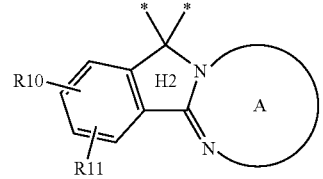

G2

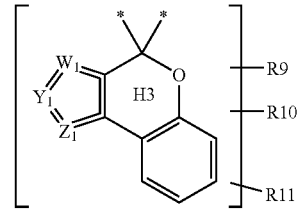

G3

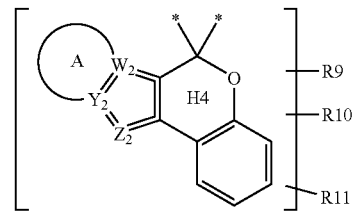

G4

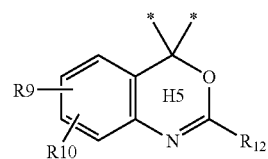

G5

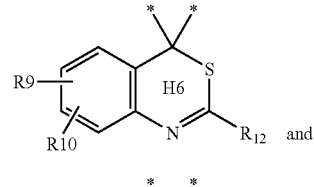

G6 and

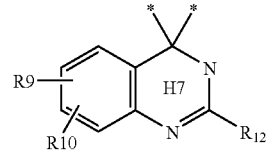

G7 wherein:
$Y_1$, $W_1$ and $Z_1$, on the one hand, and $Y_2$, $W_2$ and $Z_2$, on the other hand, are chosen from, independently of one another, carbon atoms, nitrogen atoms, sulphur atoms and divalent groups $CR_{13}$ and $NR_{13}$;

$R_9$, $R_{10}$, $R_{11}$ and $R_{13}$ have the same definitions as $R_1$;

$R_{12}$ is chosen from:
hydrogen atoms;
$C_1$-$C_9$ alkyl radicals;
amino radicals;
$C_1$-$C_9$ alkoxy radicals;

$C_6$-$C_{18}$ aryl radicals, which are unsubstituted or substituted by at least one group chosen from hydrogen atoms, hydroxyl radicals, $C_1$-$C_9$ alkyl radicals, $C_6$-$C_{18}$ aryl radicals, $C_6$-$C_{18}$ aryloxy radicals, $C_1$-$C_9$ alkoxy radicals, halo radicals, carboxyl radicals, cyano radicals and amino radicals which are substituted or unsubstituted;

furanyl radicals;

($C_1$-$C_9$)alkylthio radicals;

thienyl radicals;

phenylcarbonyl radicals;

trifluoroalkyl radicals; and di($C_6$-$C_{18}$)aryl($C_1$-$C_9$)alkyl radicals; and A represents a $C_6$-$C_{18}$ aryl group or a heterocyclic group which is saturated or unsaturated, substituted or unsubstituted, comprising from 5 to 12 ring members, and, in at least one second compartment, at least one acidifying agent or at least one basifying agent.

18. The multi-compartment kit according to claim 17, comprising, in the at least one second compartment, at least one acidifying agent, and in at least one third compartment, at least one basifying agent.

19. The composition according to claim 1, further comprising at least one surfactant and at least one polymer.

20. The composition according to claim 19, wherein the at least one surfactant is chosen from anionic, cationic, nonionic, amphoteric and zwitterionic surfactants.

21. The composition according to claim 19, wherein the at least one polymer is chosen from associative and non-associative thickening polymers.

22. The composition according to claim 1, wherein the composition is appropriate for coloring human hair.

* * * * *

UNITED STATES PATENT AND TRADEMARK OFFICE
CERTIFICATE OF CORRECTION

PATENT NO. : 7,641,703 B2
APPLICATION NO. : 12/076566
DATED : January 5, 2010
INVENTOR(S) : Frederic Guerin et al.

It is certified that error appears in the above-identified patent and that said Letters Patent is hereby corrected as shown below:

In claim 6, col. 50, line 9, "OH groups" should read -- CH groups --.

In claim 16, col. 116, line 2, "X(OH)" should read -- $X(OH)_n$ --.

Signed and Sealed this
Ninth Day of August, 2011

David J. Kappos
*Director of the United States Patent and Trademark Office*